(12) United States Patent
Guan et al.

(10) Patent No.: US 8,975,238 B2
(45) Date of Patent: Mar. 10, 2015

(54) COMPOSITIONS COMPRISING S-ADENOSYLMETHIONINE AND A GALLIC ACID ESTER

(71) Applicant: Methylation Sciences International SRL, Christ Church (BB)

(72) Inventors: Dechi Guan, Vancouver (CA); I. David MacDonald, Surrey (CA)

(73) Assignee: Methylation Sciences International SRL, Christ Church (BB)

( * ) Notice: Subject to any disclaimer, the term of this patent is extended or adjusted under 35 U.S.C. 154(b) by 0 days.

(21) Appl. No.: 14/247,061

(22) Filed: Apr. 7, 2014

(65) Prior Publication Data
US 2014/0220129 A1   Aug. 7, 2014

Related U.S. Application Data

(63) Continuation of application No. PCT/CA2013/000876, filed on Oct. 16, 2013.

(60) Provisional application No. 61/715,138, filed on Oct. 17, 2012.

(51) Int. Cl.
| | | |
|---|---|---|
| *A61K 31/7076* | (2006.01) | |
| *A61K 31/235* | (2006.01) | |
| *A61K 9/28* | (2006.01) | |
| *A61K 47/14* | (2006.01) | |
| *A61K 9/20* | (2006.01) | |
| *A61K 9/48* | (2006.01) | |

(52) U.S. Cl.
CPC ........... *A61K 31/7076* (2013.01); *A61K 31/235* (2013.01); *A61K 47/14* (2013.01); *A61K 9/2054* (2013.01); *A61K 9/2059* (2013.01); *A61K 9/4866* (2013.01); *A61K 9/28* (2013.01)

USPC .............................................. 514/46; 514/544

(58) Field of Classification Search
None
See application file for complete search history.

(56) References Cited

U.S. PATENT DOCUMENTS

| | | |
|---|---|---|
| 3,893,999 A | 7/1975 | Fiecchi |
| 4,956,173 A | 9/1990 | Le Fur et al. |

(Continued)

FOREIGN PATENT DOCUMENTS

| | | |
|---|---|---|
| CA | 2364063 | 9/2000 |
| CA | 2677053 | 8/2008 |

(Continued)

OTHER PUBLICATIONS

International Search Report and Written Opinion dated Dec. 5, 2013 for PCT/CA13/000876, 13 pages.

(Continued)

*Primary Examiner* — Bethany Barham
*Assistant Examiner* — Barbara Frazier
(74) *Attorney, Agent, or Firm* — Wilson Sonsini Goodrich & Rosati

(57) ABSTRACT

Provided herein are compositions and formulations comprising S-adenosyl-L-methionine ("SAM-e" or "SAMe") and one or more gallic acid esters. Also provided herein are methods for improving the delivery of SAMe. Compositions and formulations provided herein increase SAMe plasma concentrations and area under the curve (AUC) values. Also provided herein are methods of treating a disease or disorder in a subject by administering compositions or formulations comprising exogenous SAMe and one or more gallic acid esters.

11 Claims, 5 Drawing Sheets

(56) References Cited

U.S. PATENT DOCUMENTS

| | | | |
|---|---|---|---|
| 5,128,249 | A | 7/1992 | Gennari |
| 5,962,522 | A | 10/1999 | Wacher et al. |
| 6,004,575 | A | 12/1999 | Luessen et al. |
| 6,180,666 | B1 | 1/2001 | Wacher et al. |
| 7,303,762 | B2 | 12/2007 | New |
| 7,651,995 | B2 | 1/2010 | New |
| 8,314,058 | B2 | 11/2012 | New |
| 2002/0164369 | A1 | 11/2002 | Rao et al. |
| 2006/0013905 | A1 | 1/2006 | Tehoharides |
| 2007/0265211 | A1 | 11/2007 | Rath et al. |
| 2009/0088404 | A1 | 4/2009 | Freedman et al. |
| 2010/0056627 | A1 | 3/2010 | Higuchi et al. |
| 2011/0027342 | A1 | 2/2011 | MacDonald et al. |
| 2011/0027360 | A1 | 2/2011 | Harrison et al. |
| 2012/0177602 | A1 | 7/2012 | New |

FOREIGN PATENT DOCUMENTS

| | | |
|---|---|---|
| CA | 2769682 | 2/2010 |
| CA | 2769490 | 2/2011 |
| CA | 2769582 | 2/2011 |
| WO | WO 2012-012902 | 2/2012 |
| WO | WO2014-059522 | 4/2014 |

OTHER PUBLICATIONS

Baldrick, P. "Pharmaceutical Excipient Development: The Need for Preclinical Guidance," Regul Toxicol Pharmacology 32, 210-218 (2000).

Stewart, B. "Comparison of Intestinal Permeabilities Determined in Multiple in Vitro and in Situ Models: Relationship to Absorption in Humans," Pharmaceutical Research, vol. 12, No. 5, 693-699 (1995).

Caro and Cederbaum (2005) Biochemical Pharmacology 69:1081-1093 "Inhibition of CYP2E1 catalytic activity in vitro by S-adenosyl-L-methionine".

Feng et al. (2003) Mutation Research. May 9; 537(1):101-108. "Correlation of antimutagenic activity and suppression of CYP1A with the lipophilicity of alkyl gallates and other phenolic compounds".

Authors Unknown. (2007) International Journal of Toxicology. 26 Suppl 3:89-118 "Final report on the amended safety assessment of Propyl Gallate".

Price et al. (2008) Xenobiotica. Jun.; 38(6):574-86. "Effect of butylated hydroxytoluene, curcumin, propyl gallate and thiabendazole on cytochrome P450 forms in cultured human hepatocytes".

EP 13834351.2 European Search Report dated Jul. 31, 2014.

"New S-Adenosilmethionine Salts and the Process for their Preparation", Research Disclosure, Mason Publication, Hampshire, GB, vol. 332, Dec. 1, 1991, 927-933.

COMPOSITIONS COMPRISING S-ADENOSYLMETHIONINE AND A GALLIC ACID ESTER

CROSS REFERENCE TO RELATED APPLICATIONS

This application is a continuation of International Patent Application No. PCT/CA2013/000876, filed Oct. 16, 2013, which claims the benefit of U.S. Provisional Application No. 61/715,138, filed Oct. 17, 2012, both of which are incorporated herein by reference in their entireties.

BACKGROUND OF THE INVENTION

S-adenosyl-L-methionine ("SAM-e" or "SAMe") is a naturally occurring compound that is present in almost every tissue throughout the body. Aside from water, SAMe is considered the second most common metabolic molecule—adenosine triphosphate (ATP) being the most common. SAMe is available as an over-the-counter dietary supplement in a number of countries and by prescription in Europe. Supplementation with exogenous SAMe has been tested and showed efficacious for the treatment of various ailments, including arthritis, Alzheimer's, liver disease and depression. Unfortunately, however, the uptake of exogenous SAMe is very low (<5%) and therefore large doses are required daily. Thus, there is a need for enhancing the delivery and thus efficacy of exogenous SAMe.

SUMMARY OF THE INVENTION

Provided herein are compositions, formulations, medicaments, uses, and methods for enhancing the delivery of exogenous S-Adenosyl-L-Methionine ("SAMe"). Also provided herein are compositions, formulations, medicaments, uses, and methods for increasing SAMe plasma levels. In certain embodiments, compositions, formulations, medicaments, uses, and methods described herein provide improved SAMe levels in vivo as compared to conventional dosage forms of SAMe.

In certain embodiments, provided herein are compositions, formulations, or medicaments comprising exogenous SAMe and one or more gallic acid ester. In some embodiments, a gallic acid ester provided herein is selected from the group consisting of methyl gallate, ethyl gallate, propyl gallate, butyl gallate, isobutyl gallate, isoamyl gallate, octyl gallate, dodecyl gallate, lauryl gallate, hexadecyl gallate, cetyl gallate, gallocatechol, gallocatechin, and epigallocatechin. In some embodiments, a gallic acid ester provided herein is ethyl gallate, isoamyl gallate, propyl gallate or octyl gallate.

In some embodiments, a gallic acid ester provided herein is ethyl gallate.

In some embodiments, a gallic acid ester provided herein is isoamyl gallate.

In some embodiments, a gallic acid ester provided herein is octyl gallate.

In a preferred embodiment, a gallic acid ester provided herein is propyl gallate.

In certain embodiments, compositions, formulations, medicaments, uses, and methods described herein provide improved SAMe levels in vivo as compared to conventional dosage forms of SAMe which lack gallic acid esters.

In some embodiments, provided herein are compositions, formulations, or medicaments comprising exogenous SAMe and one or more gallic acid esters, wherein the ratio (weight:weight) of said gallic acid ester to S-adenosylmethionine is from 5:1 to 1:400. In some embodiments, the ratio (weight:weight) of said gallic acid ester to S-adenosylmethionine is from 5:1 to 1:400. In some embodiments, the ratio (weight:weight) of said gallic acid ester to S-adenosylmethionine is from 5:1 to 1:100. In some embodiments, the ratio (weight:weight) of said gallic acid ester to S-adenosylmethionine is from 1:1 to 1:100. In some embodiments, the ratio (weight:weight) of said gallic acid ester to S-adenosylmethionine is from 1:2 to 1:80. In some embodiments, the ratio (weight:weight) of said gallic acid ester to S-adenosylmethionine is from 1:4 to 1:64. In some embodiments, the ratio (weight:weight) of said gallic acid ester to S-adenosylmethionine is from 4:1 to 1:80. In some embodiments, the ratio (weight:weight) of said gallic acid ester to S-adenosylmethionine is from 3:1 to 1:60. In some embodiments, the ratio (weight:weight) of said gallic acid ester to S-adenosylmethionine is from 2:1 to 1:40. In some embodiments, the ratio (weight:weight) of said gallic acid ester to S-adenosylmethionine is from 1:1 to 1:16. In some embodiments, the inventors have surprisingly discovered that ratios of gallic acid ester to SAMe may be optimized for different gallic acid esters. In some embodiments, provided herein are compositions comprising exogenous SAMe and ethyl gallate, isoamyl gallate or octyl gallate, wherein the weight ratio of ethyl gallate, isoamyl gallate or octyl gallate to SAMe is from 1:1 to 1:16. In some embodiments, provided herein are compositions comprising exogenous SAMe and ethyl gallate, wherein the weight ratio of ethyl gallate:SAMe is from about 1:1 to 1:100. In some embodiments, provided herein are compositions comprising exogenous SAMe and isoamyl gallate, wherein the weight ratio of isoamyl gallate:SAMe is from about 1:1 to 1:100. In some embodiments, provided herein are compositions comprising exogenous SAMe and octyl gallate, wherein the weight ratio of octyl gallate:SAMe is from about 1:1 to 1:100. In some embodiments, provided herein are compositions comprising exogenous SAMe and propyl gallate, wherein the weight ratio of propyl gallate:SAMe is from about 1:1 to 1:100. In some embodiments, provided herein are compositions comprising exogenous SAMe and propyl gallate, wherein the weight ratio of propyl gallate:SAMe is from about 1:2 to 1:80. In some embodiments, provided herein are compositions comprising exogenous SAMe and propyl gallate, wherein the weight ratio of propyl gallate:SAMe is from about 1:4 to 1:64. In some embodiments, provided herein are compositions comprising exogenous SAMe and propyl gallate, wherein the weight ratio of propyl gallate:SAMe is from about 1:1 to 1:16. In some embodiments, the gallic acid ester is propyl gallate and the weight ratio of propyl gallate:SAMe is from 1:1 to 1:2, 1:2 to 1:3, 1:3 to 1:4, 1:4 to 1:5, 1:5 to 1:6, 1:6 to 1:7, 1:7 to 1:8, 1:8 to 1:9, 1:9 to 1:10, 1:10 to 1:11, 1:11 to 1:12, 1:12 to 1:13, 1:13 to 1:14, 1:14 to 1:15, or 1:15 to 1:16. In some embodiments, the gallic acid ester is propyl gallate and the weight ratio of propyl gallate:SAMe is about 1:16.

In some embodiments, provided herein are compositions comprising exogenous SAMe and propyl gallate, wherein the weight ratio of propyl gallate:SAMe is from about 1:4 to 1:64.

In some embodiments, the ratio (weight:weight) of said gallic acid ester to S-adenosylmethionine is from 1:1 to 1:64.

In some embodiments, the ratio (weight:weight) of said gallic acid ester to S-adenosylmethionine is from 1:1 to 1:16.

In some embodiments, provided herein are formulations comprising exogenous SAMe and one or more gallic acid ester, comprising about 1 to about 200 mg of gallic acid ester. In some embodiments, said formulations comprise about 1 to about 150 mg of gallic acid ester. In some embodiments, said formulations comprise about 5 to about 100 mg of gallic acid ester. In some embodiments, said formulations comprise about 1 to about 5 mg of gallic acid ester. In some embodiments, said formulations comprise about 5 to about 10 mg, about 10 to about 50 mg, about 50 to about 100 mg, about 100 to about 150 mg, about 150 to about 200 mg, about 200 to about 250 mg, about 250 to about 300 mg, about 300 to about 350 mg, about 350 to about 400 mg or greater than about 400 mg gallic acid ester.

In some embodiments, said formulations comprise about 1 to about 100 mg of gallic acid ester.

In some embodiments, said formulations comprise about 1 to about 50 mg of gallic acid ester.

In some embodiments, said formulations comprise about 10 to about 50 mg of gallic acid ester.

In some embodiments, said formulations comprise about 25 mg of gallic acid ester.

In some embodiments, provided herein are compositions and formulations comprising exogenous SAMe and one or more gallic acid ester, wherein said composition comprises 0.1 to 80% by weight gallic acid ester. In some embodiments, said compositions or formulations comprise 0.1 to 70% by weight gallic acid ester. In some embodiments, said compositions or formulations comprise 0.1 to 60% by weight gallic acid ester. In some embodiments, said compositions or formulations comprise 0.1 to 50% by weight gallic acid ester. In some embodiments, said compositions or formulations comprise 0.1 to 40% by weight gallic acid ester. In some embodiments, said compositions or formulations comprise 0.1 to 30% by weight gallic acid ester. In some embodiments, said compositions or formulations comprise 0.1 to 20% by weight gallic acid ester. In some embodiments, said compositions or formulations comprise 0.1 to 10% by weight gallic acid ester. In some embodiments, said compositions or formulations comprise 0.5 to 10% by weight gallic acid ester. In some embodiments, said compositions or formulations comprise 0.5 to 5% by weight gallic acid ester. In some embodiments, said compositions or formulations comprise 0.5 to 2.5% by weight gallic acid ester. Other exemplary embodiments comprise from 0.25 to 1%, 1 to 2%, 2 to 3%, 3 to 4%, 4 to 5%, 5 to 10%, 10 to 15%, 15 to 20%, 20 to 25%, 25 to 30%, 30 to 35%, 35 to 40%, 40 to 50%, 50 to 60%, 60 to 70%, 70 to 80% or greater than 80% by weight gallic acid ester. The percentage by weight is based on the weight of the total dosage form.

In some embodiments, said compositions or formulations comprise 0.5 to 5% by weight gallic acid ester.

In some embodiments, said compositions or formulations comprise 0.5 to 2.5% by weight gallic acid ester.

In some embodiments, provided herein are compositions and formulations comprising exogenous SAMe and one or more gallic acid ester, comprising about 10 to about 1200 mg of SAMe. In some embodiments, said compositions or formulations comprise about 100 to about 1000 mg of SAMe. In some embodiments, said compositions or formulations comprise about 100 to about 800 mg of SAMe. In some embodiments, said compositions or formulations comprise about 100 to about 600 mg of SAMe. In some embodiments, said compositions or formulations comprise about 100 to about 500 mg of SAMe. In some embodiments, said compositions or formulations comprise about 100 to about 400 mg of SAMe.

In some embodiments, said compositions or formulations comprise about 100 mg of SAMe. In some embodiments, said compositions or formulations comprise about 200 mg of SAMe. In some embodiments, said compositions or formulations comprise about 400 mg of SAMe. In some embodiments, said compositions or formulations comprise about 600 mg of SAMe. In some embodiments, said compositions or formulations comprise about 800 mg of SAMe. In some embodiments, said compositions or formulations comprise about 1000 mg of SAMe. In some embodiments, said compositions or formulations comprise about 1200 mg of SAMe. In some embodiments, said compositions or formulations comprise about 1600 mg of SAMe. In some embodiments, said compositions or formulations comprise about 3200 mg of SAMe. In some embodiments, said compositions or formulations comprise about 3600 mg of SAMe. When referring to the amount of SAMe it is intended to mean the SAMe ion.

In some embodiments, said compositions or formulations comprise about 400 mg of SAMe.

In some embodiments, provided herein are compositions and formulations comprising exogenous SAMe and one or more gallic acid ester, wherein said composition comprises at least 10% by weight SAMe. In some embodiments, said compositions or formulations comprise at least 20% by weight SAMe. In some embodiments, said compositions or formulations comprise at least 30% by weight SAMe. In some embodiments, said compositions or formulations comprise at least 40% by weight SAMe. In some embodiments, said compositions or formulations comprise at least 50% by weight SAMe. In some embodiments, said compositions or formulations comprise at least 60% by weight SAMe. In some embodiments, said compositions or formulations comprise at least 70% by weight SAMe. In some embodiments, said compositions or formulations comprise at least 80% by weight SAMe. In some embodiments, said compositions or formulations comprise at least 90% by weight SAMe. In some embodiments, said compositions or formulations comprise from about 10 to 90% by weight SAMe. In some embodiments, said compositions or formulations comprise from about 20 to 80% by weight SAMe. In some embodiments, said compositions or formulations comprise from about 30 to 70% by weight SAMe. In some embodiments, said compositions or formulations comprise from about 30 to 60% by weight SAMe. In some embodiments, said compositions or formulations comprise from about 30 to 50% by weight SAMe. In some embodiments, said compositions or formulations comprise from about 30 to 40% by weight SAMe. When referring to the percent by weight of SAMe it is intended to mean the SAMe ion.

In some embodiments, SAMe is a SAMe disulfate tosylate salt or a SAMe 1,4-butanedisulfonate salt.

In preferred embodiments, SAMe is a SAMe disulfate tosylate salt.

In some embodiments, provided herein are compositions which provide increased plasma SAMe levels. In some embodiments, the composition when administered to a selected subject group provides in said selected subject group an average maximum SAMe blood plasma concentration (average $C_{max}$) of at least about 120 ng/mL per each 100 mg of SAMe ion, or of at least about 130 ng/mL per each 100 mg of SAMe ion, or of at least about 150 ng/mL per each 100 mg of SAMe ion, or of at least about 175 ng/mL per each 100 mg of SAMe ion, or of at least about 200 ng/mL per each 100 mg of SAMe ion, or of at least about 225 ng/mL per each 100 mg of SAMe ion or of at least about 250 ng/mL per each 100 mg of SAMe ion, or of at least about 300 ng/mL per each 100 mg of SAMe ion. In some embodiments, the composition when administered to a selected subject group provides in said selected subject group an average SAMe $C_{max}$ of at least about 120 ng/mL per each 100 mg of SAMe ion. In some embodiments, the composition when administered to a selected subject group provides in said selected subject group an average SAMe $C_{max}$ of at least about 130 ng/mL per each 100 mg of SAMe ion. In some embodiments, the composition when administered to a selected subject group provides in said selected subject group an average SAMe $C_{max}$ of at least about 135 ng/mL per each 100 mg of SAMe ion. In some embodiments, the composition when administered to a selected subject group provides in said selected subject group an average SAMe $C_{max}$ of at least about 140 ng/mL per each 100 mg of SAMe ion. In some embodiments, the composition when administered to a selected subject group provides in said selected subject group an average SAMe $C_{max}$ of at least about 145 ng/mL per each 100 mg of SAMe ion.

In some embodiments, the composition when administered to a selected subject group provides in said selected subject group an average maximum SAMe blood plasma concentration (average $C_{max}$) of at least about 120 ng/mL per each 100 mg of SAMe ion.

In some embodiments, the composition when administered to a selected subject group provides in said selected subject group an average SAMe $C_{max}$ of at least about 12 ng/mL, at least about 13 ng/mL, at least about 15 ng/mL, at least about 17.5 ng/mL, at least about 20 ng/mL, at least about 22.5 ng/mL, at least about 25 ng/mL, or at least about 30 ng/mL per each 10 mg of SAMe ion. In other embodiments, the composition when administered to a selected subject group provides in said selected subject group an average SAMe Cmax of at least about 1.2 ng/mL, at least about 1.3 ng/mL, at least about 1.35 ng/mL, at least about 1.5 ng/mL, at least about 1.75 ng/mL, at least about 2.0 ng/mL, at least about 2.25 ng/mL, at least about 2.5 ng/mL, or at least about 3.0 ng/mL per each 1 mg of SAMe ion. In some embodiments, the composition when administered to a selected subject group provides in said selected subject group an average SAMe $C_{max}$ of at least about 12 ng/mL per each 1 mg of SAMe ion. In some embodiments, the composition when administered to a selected subject group provides in said selected subject group an average SAMe $C_{max}$ of at least about 13 ng/mL per each 1 mg of SAMe ion. In some embodiments, the composition when administered to a selected subject group provides in said selected subject group an average SAMe $C_{max}$ of at least about 14 ng/mL per each 1 mg of SAMe ion. In some embodiments, the composition when administered to a selected subject group provides in said selected subject group an average SAMe $C_{max}$ of at least about 14.5 ng/mL per each 1 mg of SAMe ion.

In some embodiments, the composition when administered to a selected subject group provides in said selected subject group an average SAMe $C_{max}$ of at least about 12 ng/mL per each 10 mg of SAMe ion.

In preferred embodiments, the gallic acid ester is propyl gallate. In some embodiments, provide herein are compositions comprising SAMe and propyl gallate, wherein said compositions when administered to a selected subject group provides in said selected subject group an average SAMe Cmax of at least about 1.2 ng/mL, at least about 1.3 ng/mL, at least about 1.35 ng/mL, at least about 1.5 ng/mL, at least about 1.75 ng/mL, at least about 2.0 ng/mL, at least about 2.25 ng/mL, at least about 2.5 ng/mL, or at least about 3.0 ng/mL per each 1 mg of SAMe ion. In some embodiments, provide herein are compositions comprising SAMe and propyl gallate, wherein said compositions when administered to a selected subject group provides in said selected subject group an average SAMe $C_{max}$ of at least about 12 ng/mL per each 1 mg of SAMe ion. In some embodiments, provide herein are compositions comprising SAMe and propyl gallate, wherein said compositions when administered to a selected subject group provides in said selected subject group an average SAMe $C_{max}$ of at least about 13 ng/mL per each 1 mg of SAMe ion. In some embodiments, provide herein are compositions comprising SAMe and propyl gallate, wherein said compositions when administered to a selected subject group provides in said selected subject group an average SAMe $C_{max}$ of at least about 14 ng/mL per each 1 mg of SAMe ion. In some embodiments, provide herein are compositions comprising SAMe and propyl gallate, wherein said compositions when administered to a selected subject group provides in said selected subject group an average SAMe $C_{max}$ of at least about 14.5 ng/mL per each 1 mg of SAMe ion.

In some embodiments, provide herein are compositions comprising SAMe and propyl gallate, wherein said compositions when administered to a selected subject group provides in said selected subject group an average SAMe Cmax of at least about 1.2 ng/mL per each 1 mg of SAMe ion.

In some embodiments, provided herein are compositions which when administered to a selected subject group provides in said selected subject group an average AUC of at least about 800 ng·h/mL per each 100 mg dosage of SAMe ion, or of at least about 850 ng·h/mL per each 100 mg dosage of SAMe ion, or at least about 900 ng·h/mL per each 100 mg dosage of SAMe ion, at least about 950 ng·h/mL per each 100 mg dosage of SAMe ion, or at least about 1000 ng·h/mL per each 100 mg dosage of SAMe ion. In some embodiments, the compositions when administered to a selected subject group provides in said selected subject group an average AUC of at least about 800 ng·h/mL per each 100 mg dosage of SAMe ion. In some embodiments, the compositions when administered to a selected subject group provides in said selected subject group an average AUC of at least about 850 ng·h/mL per each 100 mg dosage of SAMe ion. In some embodiments, the compositions when administered to a selected subject group provides in said selected subject group an average AUC of at least about 900 ng·h/mL per each 100 mg dosage of SAMe ion. In some embodiments, the compositions when administered to a selected subject group provides in said selected subject group an average AUC of at least about 950 ng·h/mL per each 100 mg dosage of SAMe ion. In some embodiments, the compositions when administered to a selected subject group provides in said selected subject group an average AUC of at least about 1000 ng·h/mL per each 100 mg dosage of SAMe ion.

In some embodiments, provided herein are compositions which when administered to a selected subject group provides in said selected subject group an average AUC of at least about 800 ng·h/mL per each 100 mg dosage of SAMe ion.

In some embodiments, the composition when administered to a selected subject group provides in said selected subject group an average SAMe AUC of at least about 80 ng·h/mL, at least about 85 ng·h/mL, at least about 90 ng·h/mL, at least about 95 ng·h/mL, or at least about 100 ng·h/mL per each 10 mg of SAMe ion.

In some embodiments, the composition when administered to a selected subject group provides in said selected subject group an average SAMe AUC of at least about 80 ng·h/mL per each 10 mg of SAMe ion.

In other embodiments, the composition when administered to a selected subject group provides in said selected subject group an average SAMe AUC of at least about 8 ng·h/mL, at least about 8.5 ng·h/mL, at least about 9 ng·h/mL, at least about 9.5 ng·h/mL, or at least about 10 ng·h/mL per each 1 mg of SAMe ion. In some embodiments, the compositions when administered to a selected subject group provides in said selected subject group an average AUC of at least about 8 ng·h/mL per each 1 mg dosage of SAMe ion. In some embodiments, the compositions when administered to a selected subject group provides in said selected subject group an average AUC of at least about 8.5 ng·h/mL per each 1 mg dosage of SAMe ion. In some embodiments, the compositions when administered to a selected subject group provides in said selected subject group an average AUC of at least about 9 ng·h/mL per each 1 mg dosage of SAMe ion. In some embodiments, the compositions when administered to a selected subject group provides in said selected subject group an average AUC of at least about 9.5 ng·h/mL per each 1 mg dosage of SAMe ion. In some embodiments, the compositions when administered to a selected subject group provides in said selected subject group an average AUC of at least about 10 ng·h/mL per each 1 mg dosage of SAMe ion.

In other embodiments, the composition when administered to a selected subject group provides in said selected subject group an average SAMe AUC of at least about 8 ng·h/mL per each 1 mg of SAMe ion.

In preferred embodiments, the gallic acid ester is propyl gallate. In some embodiments, provide herein are compositions comprising SAMe and propyl gallate, wherein said compositions when administered to a selected subject group provides in said selected subject group an average SAMe AUC of at least about 8 ng·h/mL, at least about 8.5 ng·h/mL, at least about 9 ng·h/mL, at least about 9.5 ng·h/mL, or at least about 10 ng·h/mL per each 1 mg of SAMe ion. In some embodiments, provide herein are compositions comprising SAMe and propyl gallate, wherein said compositions when administered to a selected subject group provides in said selected subject group an average AUC of at least about 8 ng·h/mL per each 1 mg dosage of SAMe ion. In some embodiments, provide herein are compositions comprising SAMe and propyl gallate, wherein said compositions when administered to a selected subject group provides in said selected subject group an average AUC of at least about 8.5 ng·h/mL per each 1 mg dosage of SAMe ion. In some embodiments, provide herein are compositions comprising SAMe and propyl gallate, wherein said compositions when administered to a selected subject group provides in said selected subject group an average AUC of at least about 9 ng·h/mL per each 1 mg dosage of SAMe ion. In some embodiments, provide herein are compositions comprising SAMe and propyl gallate, wherein said compositions when administered to a selected subject group provides in said selected subject group an average AUC of at least about 9.5 ng·h/mL per each 1 mg dosage of SAMe ion. In embodiments, provide herein are compositions comprising SAMe and propyl gallate, wherein said compositions when administered to a selected subject group provides in said selected subject group an average AUC of at least about 10 ng·h/mL per each 1 mg dosage of SAMe ion.

In some embodiments, provide herein are compositions comprising SAMe and propyl gallate, wherein said compositions when administered to a selected subject group provides in said selected subject group an average SAMe AUC of at least about 8 ng·h/mL per each 1 mg of SAMe ion.

In some embodiments, the exogenous SAMe ion dose administered is at least 10 mg. In some embodiments, the exogenous SAMe ion dose administered is from 10 to 3600 mg. In some embodiments, the composition when administered to a selected subject group provides in said selected subject group an average SAMe Cmax of at least about 120 ng/mL and an average AUC of at least about 800 ng·h/mL per each 100 mg of SAMe ion for doses of SAMe ion of at least 100 mg. In other embodiments, the composition when administered to a selected subject group provides in said selected subject group an average SAMe Cmax of at least about 130 ng/mL and an average AUC of at least about 850 ng·h/mL per each 100 mg of SAMe ion for doses of SAMe ion of at least 100 mg. In still other preferred embodiments, the composition when administered to a selected subject group provides in said selected subject group an average SAMe Cmax of at least about 12 ng/mL and an average AUC of at least about 90 ng·h/mL per each 10 mg of SAMe ion for doses of SAMe ion of at least 10 mg. In some embodiments, the composition when administered to a selected subject group provides in said selected subject group an average SAMe Cmax of at least about 13 ng/mL and an average AUC of at least about 90 ng·h/mL per each 10 mg of SAMe ion for doses of SAMe ion of at least 10 mg. In other embodiments, the composition when administered to a selected subject group provides in said selected subject group an average SAMe Cmax of at least about 1.2 ng/mL and/or an average AUC of at least about 9 ng·h/mL per each 1 mg of SAMe ion. In some embodiments, the composition when administered to a selected subject group provides in said selected subject group an average SAMe Cmax of at least about 1.3 ng/mL and/or an average AUC of at least about 9 ng·h/mL per each 1 mg of SAMe ion. In some embodiments, provided herein are compositions comprising SAMe and propyl gallate which when administered to a selected subject group provide in said selected subject group an average SAMe Cmax of at least about 1.4 ng/mL and/or an average AUC of at least about 9 ng·h/mL per each 1 mg of SAMe ion. In other embodiments, provided herein are compositions comprising SAMe and propyl gallate which when said compositions are administered to a selected subject group provide in said selected subject group an average SAMe Cmax of at least about 1.5 ng/mL and/or an average AUC of at least about 9 ng·h/mL per each 1 mg of SAMe ion. In additional embodiments, provided herein are compositions comprising SAMe and propyl gallate which when said compositions are administered to a selected subject group provide in said selected subject group an average SAMe Cmax of at least about 1.3 ng/mL and/or an average AUC of at least about 9.5 ng·h/mL per each 1 mg of SAMe ion. In other embodiments, provided herein are compositions comprising SAMe and propyl gallate which when said compositions are administered to a selected subject group provide in said selected subject group an average SAMe Cmax of at least about 1.3 ng/mL and/or an average AUC of at least about 10.0 ng·h/mL per each 1 mg of SAMe ion.

In some embodiments, provided herein are compositions which provide in the subject one of an average Tmax or Cmax with reduced variation or a reduced effective dose in comparison to a SAMe control group. SAMe control groups are those wherein the subject or selected subject group is administered the same or similar SAMe formulation with the exception that the one or more gallic acid ester is not present.

In some embodiments, provided herein are compositions which when administered to a selected subject group provide in said selected subject group an improved SAMe pharmacokinetic profile such that once a day dosing using compositions described herein is equivalent (or better) to bi-daily dosing of conventional SAMe compositions that do not contain at least one gallic acid ester. "Improved SAMe pharmacokinetic profile" can be measured by, for example, an equivalent or higher SAMe AUC or Cmax, a reduced variation of SAMe Tmax, a reduced side effect profile, and/or an increased rate of onset. In some embodiments, provided herein are compositions comprising SAMe and propyl gallate wherein once a day administration of said compositions to a selected subject group provides in said selected subject group an improved SAMe pharmacokinetic profile in comparison to a SAMe control group.

In some exemplary embodiments, a functional coating acts to co-deliver exogenous SAMe and the gallic acid ester to the upper small intestine where SAMe is better absorbed. In other embodiments, the functional coating results in delivery of exogenous SAMe and the gallic acid ester to the large intestine and/or colorectal regions.

In certain embodiments, provided herein are compositions comprising a unit dosage form that comprises a functional coating. Preferably, said functional coating constitutes from 1 to 20% of the total weight of the unit dosage form. In some embodiments, said functional coating comprises more than one coating layers. In certain embodiments, said functional coating comprises a seal coat and one or more additional coating layers. Preferably, said one or more additional coating layers is an enteric, time-release, non pH-dependent or pH-dependent coating. In some embodiments, said one or more additional coating layers constitutes at least 3%, 3.5%, 4%, 4.5%, 5%, or 5.5% of the total weight of the unit dosage form. More preferably, said one or more additional coating layers is an enteric coating which constitutes from 3-5% of the total weight of the unit dosage form. Most preferably, provided herein are compositions comprising SAMe and propyl gallate wherein said compositions comprise an enteric, time-release, non pH-dependent or pH-dependent coating which constitutes at least 3%, 3.5%, 4%, 4.5%, 5%, or 5.5% of the total weight of the dosage form.

In some embodiments, the composition provided herein comprises an oral dosage form or delivery system. Preferably, said oral dosage form or delivery system is a capsule or non-capsule. Most preferably, said non-capsule dosage form is a tablet. In other embodiments, the composition comprises a transdermal, transmucosal, or intramuscular dosage form. In some other embodiments, the composition comprises a dosage form for intravenous administration.

In some embodiments, the compositions provided herein comprise a minitablet. "Minitablets" or "mini-tablets" as used herein are tablets of a smaller size, typically <3 mm in diameter. Minitablets contain similar excipients as larger tablets. They are also typically made using methods similar to those used for larger tablets, such as tablet compression, seal coating and enteric coating. In some embodiments, the minitablets are filled into a capsule or pressed gently to form a larger tablet. In some embodiments, the minitablets are filled into a capsule or pressed gently to form a larger tablet along with one or more pH moderator. In some embodiments, the minitablets are filled into a capsule. In some embodiments, the minitablets are pressed into a larger tablet. In some embodiments, the minitablets are pressed into an oral disintegration tablet or "ODT". In some embodiments, the minitablets are used to reduce tablet retention within the stomach. In some embodiments, the minitablets are used to reduce side-effects associated with SAMe counter-ion(s).

In some embodiments, the minitablets are used for administration under fed conditions. In some embodiments, the minitablets are used for administration under fasted conditions. In some embodiments, administration of larger tablets exhibits a postponement in the Tmax of SAMe (or other drugs). In some embodiments, administration of the minitablet composition under fed conditions reduces postponement of the SAMe Tmax. In some embodiments, administration of the minitablet composition under fed conditions reduces retention in the stomach or a delay in gastric emptying.

In some embodiments, the minitablet composition comprises about 10 to 80% SAMe. In some embodiments, the minitablet composition comprises about 10 to 70% SAMe. In some embodiments, the minitablet composition comprises about 10 to 60% SAMe. In some embodiments, the minitablet composition comprises about 10 to 50% SAMe. In some embodiments, the minitablet composition comprises about 15 to 45% SAMe.

In some embodiments, diseases and/or disorders treatable with SAMe and gallic acid ester formulations provided herein are selected from the group consisting of, but not limited to, a mental or psychiatric disorder (e.g. psychotic/mood or non-psychotic mental disorders exemplified by depression and substance related disorders, respectively), a nervous system disease/disorder (e.g. a central nervous system disease exemplified by Alzheimer's), other neurological diseases/disorders (e.g. headaches and sleep disorders), conditions associated with injury to the central nervous system, a liver disease/disorder (e.g. alcoholic liver disease), a cancer (e.g. solid and blood-borne cancers), a joint disease/disorder (e.g. arthritis), an inflammatory disease/disorder (e.g. ulcerative colitis), an autoimmune disease/disorder (e.g. systemic lupus erythematosis and rheumatoid arthritis), a degenerative disease/disorder (e.g. Amyotrophic Lateral Sclerosis), a soft-tissue disease/disorder (e.g. a fibromyalgia disorder), a pain disease/disorder, a genetic disorder related to hyper- or hypo-methylation, a gastrointestinal disease/disorder, a cardiovascular disease/disorder, atherosclerosis, Lesch-Nyhan disease, a metabolic disease/disorder (e.g. Type 2 diabetes) and a disorder induced in whole or in part by oxidative or free-radical damage. In preferred embodiments, the composition comprises SAMe and one of ethyl gallate, isoamyl gallate, propyl gallate or octyl gallate as provided herein. In most preferred embodiments, the composition comprises SAMe and propyl gallate.

Additional embodiments provided herein relate to combinations of exogenous SAMe and one or more gallic acid ester along with one or more active ingredients that are commonly prescribed or used for treatment of and/or prophylaxis of various diseases or disorders in a subject. In preferred embodiments, the composition comprises SAMe and one of ethyl gallate, isoamyl gallate, propyl gallate or octyl gallate as provided herein. In most preferred embodiments, the composition comprises SAMe and propyl gallate.

Also provided herein are methods for treating or preventing and/or prophylaxis in a subject a disease or disorder selected from the group consisting of, but not limited to, a mental or psychiatric disorder (e.g. psychotic/mood or non-psychotic mental disorders exemplified by depression and substance related disorders, respectively), a nervous system disease/disorder (e.g. a central nervous system disease exemplified by Alzheimer's), other neurological disease/disorders (e.g. headaches and sleep disorders), conditions associated with injury to the central nervous system, a liver disease/disorder (e.g. alcoholic liver disease), a cancer (e.g. solid and blood-borne cancers), a joint disease/disorder (e.g. arthritis), an inflammatory disease/disorder (e.g. ulcerative colitis), an autoimmune disease/disorder (e.g. systemic lupus erythematosis and rheumatoid arthritis), a degenerative disease/disorder (e.g. Amyotrophic Lateral Sclerosis), a soft-tissue disease/disorder (e.g. a fibromyalgia disorder), a pain disease/disorder, a genetic disorder related to hyper- or hypo-methylation, a gastrointestinal disease/disorder, a cardiovascular disease/disorder, atherosclerosis, Lesch-Nyhan disease, and a disorder induced in whole or in part by oxidative or free-radical damage, comprising administering a composition comprising SAMe and one or more gallic acid ester, such that said disease is treated or prevented. In preferred embodiments, the composition comprises SAMe and one of ethyl gallate, isoamyl gallate, propyl gallate or octyl gallate as provided herein. In most preferred embodiments, the composition comprises SAMe and propyl gallate. Preferably, said disease or disorder is depression. Even more preferably, said depression is Major depressive disorder (also known as Major depression, Clinical depression), Dysthymic disorder (or also referred to as Dysthymia), Bipolar disorder (formerly referred to as Manic depression), Postpartum depression, Seasonal Affective Disorder (SAD), Anxiety depression, Atypical depression, Melancholic depression, Catatonic depression and Situational depression, Reactive depression, Late-Life depression (and the like), Parkinson's depression, HIV-associated depression, brief recurrent depression, Mild depression, Minor depression, Treatment-Resistant depression (TRD), co-morbid depression, or depression NOS (Not Otherwise Specified).

In some embodiments, any of the compositions provided herein is used in the treatment of the diseases and disorders described herein.

Also provided herein are methods for administering a composition comprising SAMe and a gallic acid ester wherein said method comprises administering said composition to a patient or selected subject group that have fasted prior to administration of said composition. "Fasted" typically is meant to be an overnight fast such that patients (or subjects) are administered the composition at least one hour prior to their first meal of the day (i.e. typically breakfast). Preferred "fasted" conditions are such that subjects begin fasting at least 10 or 12 hours before drug administration and fasting continues for 1 or 4 hours following drug administration. Also provided herein are methods for administering a composition comprising SAMe and a gallic acid ester wherein said method comprises administering said composition to a patient or selected subject group under fed conditions. "Fed" conditions are typically such that the patients/subjects ingest a meal approximately 1-2 hours before being administered the composition of the invention. Preferably, under "fed" conditions, subjects start fasting at least 12 hours before morning breakfast and then receive a meal (often a standardized high-fat, high-calorie meal) approximately 30 minutes before drug administration.

In some embodiments, compositions and formulations provided herein exhibit little to no gender-based pharmacokinetic effects. After administration of exogenous SAMe using formulations previously reported in the art, some of the effects of SAMe have been reported to be different in males and females. There are numerous theories regarding the reason for these gender effects. Surprisingly, compositions and formulations provided herein exhibit pharmacokinetic profiles in which there is no statistically significant difference in values between males and females. In some embodiments, provided herein are compositions and formulations which exhibit pharmacokinetic profiles that are similar in both males and females.

Also provided herein are methods for improving the uptake of SAMe, wherein said method comprises administering to a subject an exemplary composition which provides a physiologically effective amount of exogenous SAMe in combination with one or more gallic acid ester. Preferably said gallic acid ester is selected from ethyl gallate, isoamyl gallate, propyl gallate or octyl gallate. Most preferably, said gallic acid ester is propyl gallate.

Further provided herein is a method of making a formulation for improved uptake of SAMe, wherein said method comprises mixing exogenous SAMe and a gallic acid ester and formulating them into a capsule or non-capsule with or without additional excipients. Preferably said gallic acid ester is selected from ethyl gallate, isoamyl gallate, propyl gallate or octyl gallate. Most preferably, said gallic acid ester is propyl gallate.

Thus in some embodiments, provided herein is a method for improving the uptake of SAMe, wherein said method comprises administering to said subject an exemplary composition which provides a physiologically effective amount of exogenous SAMe in combination with propyl gallate. Also provided in some embodiments is a method of making a formulation for improved uptake of SAMe, wherein said method comprises combining exogenous SAMe and propyl gallate and formulating them into a capsule or non-capsule with or without additional excipients. In other embodiments, provided is a method of administering a composition comprising exogenous SAMe and propyl gallate wherein said method comprises administering said composition to a patient that has fasted for at least 10 hours prior to administration of said composition.

The details of one or more embodiments are set forth in the description below. Other features, objects and advantages will be apparent from the description, the drawings, and the claims. In addition, the disclosures of all patents and patent applications referenced herein are incorporated by reference in their entirety.

DETAILED DESCRIPTION OF THE INVENTION

Figure 1:
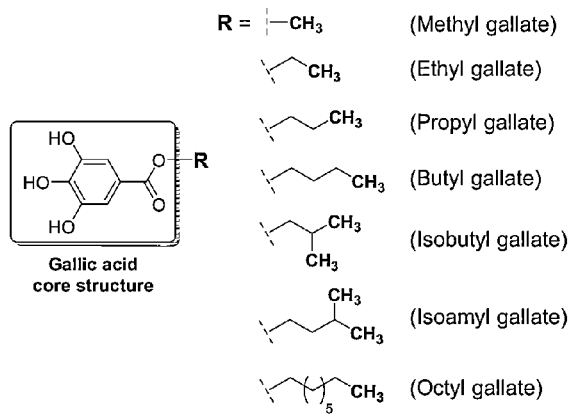
FIG. 1 is a graph of the average maximum SAMe plasma concentration (Cmax) of beagles administered a single 400 mg SAMe ion dose from one of ten different formulations: (1) a commercially available oral formulation of SAMe, (2) MSI SAMe formulation with no propyl gallate ("Control SAMe"); (3) MSI SAMe formulation co-administered with a separate 25 mg propyl gallate tablet ("Control SAMe with Separate PG"); (4) MSI SAMe formulation co-formulated with 25 mg methyl gallate; (5) MSI SAMe formulation co-formulated with 25 mg ethyl gallate; (6) MSI SAMe formulation co-formulated with 25 mg propyl gallate; (7) MSI SAMe formulation co-formulated with 25 mg butyl gallate; (8) MSI SAMe formulation co-formulated with 25 mg isobutyl gallate; (9) MSI SAMe formulation co-formulated with 25 mg isoamyl gallate; or (10) MSI SAMe formulation co-formulated with 25 mg octyl gallate.
Figure 1:
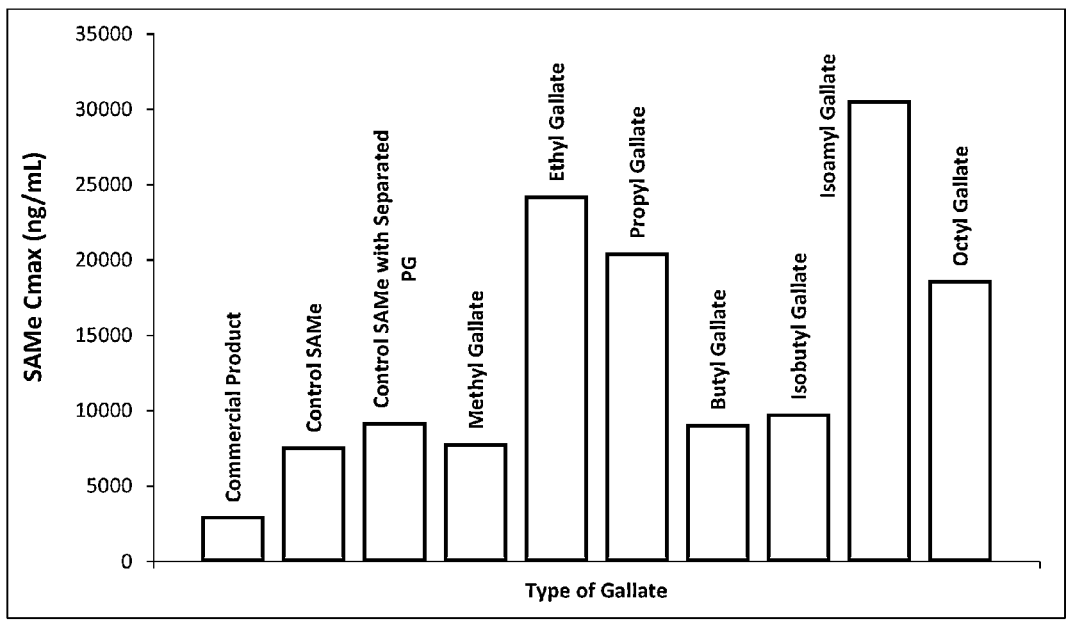

The present investigators have surprisingly discovered that the delivery of exogenous SAMe can be significantly improved when at least one gallic acid ester is administered in combination with exogenously supplied SAMe. Thus some embodiments relate to formulations comprising SAMe and one or more gallic acid ester. Other embodiments relate to compositions and methods that improve the uptake of exogenous SAMe and methods of using the same, e.g. for the treatment of various diseases or disorders in a subject and/or improving the nutritional status of a subject. Additional embodiments relate to combinations of SAMe and one or more gallic acid ester with one or more active ingredients that are commonly prescribed or used for treatment of and/or prophylaxis of various diseases or disorders in a subject. While not wishing to be bound by any one specific embodiment, provided herein is a method of increasing the absorption of SAMe wherein said one or more gallic acid ester binds to and/or interacts with said SAMe and/or the gastrointestinal tract in such a way as to increase SAMe absorption across the mucosal wall or epithelial cells of the intestine.

As used herein the term "SAMe" refers to S-adenosyl-L-methionine (or, more simply, "S-adenosylmethionine") including all of the various SAMe salts. When referring to dose or percentage, the amount (typically in mg) refers to the dose of SAMe ion administered. As mentioned above, SAMe is most commonly available as a stable salt form, e.g. with p-toluenesulfonic acid (see U.S. Pat. No. 3,893,999, incorporated herein by reference in its entirety). Other stable SAMe salts are described in, for example, U.S. Pat. No. 5,128,249, which describes particular stable salts of SAMe. Various morphologies of SAMe are suitable for use in certain embodiments provided herein. Thus, as used herein "SAMe" refers to the stable salts, amorphous forms, semicrystalline forms and crystalline forms of SAMe as well as to the ionic form of SAMe when present in vivo. Amorphous forms of SAMe can be employed at any particle size and particle size distribution.

Formulations for oral administration of exogenous SAMe are typically provided as solid or semi-solid products, dosage forms or oral delivery systems, exemplified by capsules or non-capsule dosage forms which include tablets, lozenges, gum, pastes, pellets, or granules, and generally consist of a core "matrix material" as well as one or more coatings. "Product" or "dosage form" or "oral delivery system" as used herein refers to any solid or semi-solid formulation or preparation used for oral administration and is exemplified by capsules, tablets, pastes, granules, caplets, lozenges and the like; all of which are well-known and well-documented in the art. These formulations may be administered using a clinical, pharmaceutical or veterinary dosing regimen. Oral dosage forms may also be provided as dietary or nutritional supplements or as a medical food.

"Gallates", "alkyl gallates" or "gallic acid esters" as used herein refer to salts and esters of gallic acid and have the general formula I (see below) where $R_1$ is a hydrocarbon chain which may be straight or branched. Optionally, $R_1$ group may be an alkyl, alkenyl, alkynyl, aryl, benzyl, phenyl, alicyclic, or heterocyclic group all of which groups may be substituted or unsubstituted. $R_1$ is preferably a $C_1$-$C_{22}$ alkyl group, a $C_2$-$C_{22}$ alkenyl group or a $C_2$-$C_{22}$ alkynyl group, all of which groups may be substituted or unsubstituted and may be straight chain, cyclic, cyclic unsaturated or branched chain. Moreover, this hydrocarbon chain can be a saturated, monounsaturated, or polyunsaturated. Preferably, $R_1$ is a saturated hydrocarbon chain ranging from $C_1$-$C_{22}$.

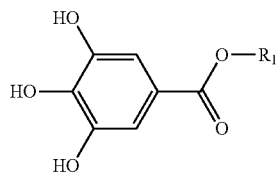

Preferred gallic acid esters for use in the invention are methyl gallate, ethyl gallate, propyl gallate, iso-propyl gallate, butyl gallate, isobutyl gallate, amyl gallate, isoamyl gallate, hexyl gallate, isohexyl gallate, heptyl gallate, isoheptyl gallate, octyl gallate, isooctyl gallate, nonyl gallate, isononyl gallate, decyl isodecyl, undecyl gallate, isoundecyl gallate, dodecyl gallate (lauryl gallate), isododecyl gallate, tridecyl gallate, isotridecyl, tetradecyl gallate, isotetradecyl gallate, pentadecyl gallate, isopentadecyl gallate, hexadecyl gallate (cetyl gallate), isohexadecyl gallate, heptadecyl gallate, isoheptadecyl gallate, octadecyl gallate, isoctadecyl gallate, cis-9-hexadecenyl (palmitoleyl) gallate, cis-9-octadecenyl (oleyl) gallate, cis,cis-9,12 octadecadienyl (linoleyl) gallate, trans,trans-9,12-octadecadienyl (linolelaidyl) gallate, cis,cis, cis-9,12,15-octadecatrienyl (linolenyl) gallate, trans,trans, trans-9,12,15-octadecatrienyl (linolenelaidyl) gallate, cis,cis, cis-6,9,12-octadecatrienyl (gamma-linolenyl) gallate, trans 9-octadecenyl (elaidyl) gallate or trans-9-hexadecenyl (palmitelaidyl) gallate. catechin gallate, epicatechin gallate, gallocatechin gallate, epigallocatechin gallate, gallocatechol gallate, 2-ethylhexyl gallate, 2-hydroxyethyl gallate, 6-O-galloylglucose, hamamelitannin, methoxyethoxyethyl m-digallate, theaflavin monogallate A &B, theaflavin digallate. More preferably, the gallic acid ester is selected from ethyl gallate, isoamyl gallate, propyl gallate or octyl gallate. Even more preferably, the gallic acid ester is considered a GRAS (Generally Recognized As Safe) substance by the U.S. Food and Drug Administration (FDA). Also preferably, the gallic acid ester has received a Novel Food approval by either the European Food Safety Authority (EFSA) or the European Medicines Agency (EMA). Most preferably, the gallic acid ester is propyl gallate. Thus provided herein are formulations comprising SAMe and propyl gallate. Propyl gallate is a preferred gallic acid ester as the investigators have shown for the first time that propyl gallate has a dose-response relationship with SAMe uptake in vivo.

In certain exemplary embodiments, the ratio (weight: weight) of gallic acid ester to exogenous SAMe is from 5:1 to 1:400. Preferably, the ratio (weight:weight) of gallic acid ester to S-adenosylmethionine is from 5:1 to 1:100, from 4:1 to 1:80, or from 1:1 to 1:16. In some preferred embodiments, the gallic acid ester is ethyl gallate, isoamyl gallate or octyl gallate and the weight ratio of ethyl gallate, isoamyl gallate or octyl gallate to SAMe is from 1:1 to 1:16. Within various embodiments, the gallic acid ester is propyl gallate and the weight ratio of propyl gallate:SAMe is from 1:1 to 1:100. In some preferred embodiments, the gallic acid ester is propyl gallate and the weight ratio of propyl gallate:SAMe is from 1:1 to 1:16. In more preferred embodiments, the gallic acid ester is propyl gallate and the weight ratio of propyl gallate: SAMe is from 1:1 to 1:2, 1:2 to 1:3, 1:3 to 1:4, 1:4 to 1:5, 1:5 to 1:6, 1:6 to 1:7, 1:7 to 1:8, 1:8 to 1:9, 1:9 to 1:10, 1:10 to 1:11, 1:11 to 1:12, 1:12 to 1:13, 1:13 to 1:14, 1:14 to 1:15, or 1:15 to 1:16. Most preferably, the gallic acid ester is propyl gallate and the weight ratio of propyl gallate:SAMe is about 1:16. Thus in some embodiments, provided is a composition comprising SAMe and propyl gallate wherein the weight ratio of propyl gallate:SAMe is from 1:1 to 1:16. Thus in some other embodiments, provided is a composition comprising SAMe and propyl gallate wherein the weight ratio of propyl gallate:SAMe is about 1:16.

In some embodiments, said composition comprising exogenous SAMe and gallic acid ester comprises from about 1 to about 5 mg, or about 5 to about 10 mg of gallic acid ester. Some other exemplary embodiments comprise about 10-50 mg gallic acid ester. Other exemplary embodiments comprise from about 50 to about 100 mg, about 100 to about 150 mg, about 150 to about 200 mg, about 200 to about 250 mg, about 250 to about 300 mg, about 300 to about 350 mg, or about 350 to about 400 mg gallic acid ester. Preferred exemplary embodiments comprise from about 5-100 mg of ethyl gallate, isoamyl gallate, propyl gallate or octyl gallate. More preferred exemplary embodiments comprise from about 5-100 mg of propyl gallate. Most preferably, compositions of the invention are administered such that the daily amount of propyl gallate dosed does not exceed the acceptable daily intake ("ADI") for propyl gallate as established by the Joint FAO/WHO Expert Committee on Food Additives (JECFA).

In some embodiments, said composition comprising exogenous SAMe and gallic acid ester comprises from 0.25 to 1%, 1 to 2%, 2 to 3%, 3 to 4%, 4 to 5%, 5 to 6% or 6 to 7% by weight gallic acid ester wherein the weight percentage is based on the weight of the total dosage form. In some other exemplary embodiments, said composition comprising SAMe and a gallic acid ester comprises 7 to 10%, 10 to 15%, 15 to 20%, 20 to 25%, 25 to 30%, 30 to 35%, 35 to 40%, 40 to 50%, 50 to 60%, 60 to 70%, 70 to 80%, or greater than 80% by weight gallic acid ester.

Some exemplary embodiments relate to "low-dose" SAMe compositions. By increasing the uptake of exogenous SAMe in the presence of a gallic acid ester, the daily administered effective dose of SAMe may be substantially lowered by administration of compositions with improved SAMe uptake in comparison to control formulations that do not contain at least one gallic acid ester. These exemplary "low-dose" treatments may enable a lower daily pill count though achieve the same or better pharmacokinetics in comparison to previously available SAMe products administered on a bi-daily or greater schedule. Some embodiments relate to administration of a selected improved dosage on a once-a-day basis. In some embodiments, the once-a-day dose may be administered in a single dosage unit exemplified by, a single tablet, capsule, or caplet. In other exemplary embodiments, the single dose may be administered as multiple tablets, capsules or caplets taken at one time. In some embodiments, for instance, a dosage of about 400 to 3600 mg of SAMe ion per day may be divided into two, three, four or more tablets, capsules or caplets of about 50 to 2000 mg, preferably about 100 to 1600 mg of SAMe per unit. In some preferred embodiments, the daily dose may comprise two, three or four units (e.g. tablets, capsules or caplets) of about 100 to 800 mg of SAMe ion per unit. Suitable dosage regimens included are: four units of about 50-400 mg of SAMe ion per unit, e.g. 50, 100, 150, 200, 250, 300, 350 or 400 mg SAMe ion per unit; three units of about 50-1000 mg of SAMe ion per unit, e.g. 50, 100, 150, 200, 250, 300, 350, 400, 450, 500, 550, 600, 650, 700, 750, 800, 850, 900, 950 or 1,000 mg of SAMe ion per unit; two units of about 50-1600 mg of SAMe ion per unit, e.g. about 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or 1600 mg of SAMe ion per unit.

SAMe exemplary formulations comprising a gallic acid ester may be configured to enable high bioavailability of the exogenous SAMe. "High bioavailability" formulations are those which provide higher average maximum SAMe blood plasma concentration (Cmax) and/or average SAMe plasma area under the curve (AUC) values in comparison to the same dosage forms of SAMe without the gallic acid ester or in comparison to other currently available commercial SAMe formulations. High bioavailability formulations when dosed to a selected subject group provide an average Cmax of at least about 100 to 130 ng/mL (and/or an average AUC of at least about 500 ng·h/mL) per each 100 mg dosage of SAMe ion. Thus in some preferred embodiments, SAMe formulations comprising one or more gallic acid ester are provided in high bioavailability SAMe formulations.

Thus, in some exemplary embodiments, the composition when administered to a selected subject group provides in said selected subject group an average SAMe Cmax (average maximum plasma concentration) of at least about 100 ng/mL per each 100 mg of SAMe ion, at least about 110 ng/mL per each 100 mg of SAMe ion, or at least about 120 ng/mL per each 100 mg of SAMe ion, or of at least about 130 ng/mL per each 100 mg of SAMe ion, or of at least about 150 ng/mL per each 100 mg of SAMe ion, or of at least about 175 ng/mL per each 100 mg of SAMe ion, or of at least about 200 ng/mL per each 100 mg of SAMe ion, or of at least about 225 ng/mL per each 100 mg of SAMe ion or of at least about 250 ng/mL per each 100 mg of SAMe ion, or of at least about 300 ng/mL per each 100 mg of SAMe ion. In some embodiments, the composition when administered to a selected subject group provides in said selected subject group an average SAMe Cmax of at least about 12 ng/mL, at least about 13 ng/mL, at least about 15 ng/mL, at least about 17.5 ng/mL, at least about 20 ng/mL, at least about 22.5 ng/mL, at least about 25 ng/mL, or at least about 30 ng/mL per each 10 mg of SAMe ion. In other embodiments, the composition when administered to a selected subject group provides in said selected subject group an average SAMe Cmax of at least about 1.2 ng/mL, at least about 1.3 ng/mL, at least about 1.35 ng/mL, at least about 1.5 ng/mL, at least about 1.75 ng/mL, at least about 2.0 ng/mL, at least about 2.25 ng/mL, at least about 2.5 ng/mL, or at least about 3.0 ng/mL per each 1 mg of SAMe ion. In preferred embodiments, the gallic acid ester is propyl gallate. Thus provide herein are compositions comprising SAMe and propyl gallate, wherein said compositions when administered to a selected subject group provides in said selected subject group an average SAMe Cmax of at least about 1.2 ng/mL, at least about 1.3 ng/mL, at least about 1.35 ng/mL, at least about 1.5 ng/mL, at least about 1.75 ng/mL, at least about 2.0 ng/mL, at least about 2.25 ng/mL, at least about 2.5 ng/mL, or at least about 3.0 ng/mL per each 1 mg of SAMe ion.

In some embodiments, the composition when administered to a selected subject group provides in said selected subject group an average AUC of at least about 800 ng·h/mL per each 100 mg dosage of SAMe ion, or of at least about 850 ng·h/mL per each 100 mg dosage of SAMe ion, or at least about 900 ng·h/mL per each 100 mg dosage of SAMe ion, at least about 950 ng·h/mL per each 100 mg dosage of SAMe ion, or at least about 1000 ng·h/mL per each 100 mg dosage of SAMe ion. In some embodiments, the composition when administered to a selected subject group provides in said selected subject group an average SAMe AUC of at least about 80 ng·h/mL, at least about 85 ng·h/mL, at least about 90 ng·h/mL, at least about 95 ng·h/mL, or at least about 100 ng·h/mL per each 10 mg of SAMe ion. In other embodiments, the composition when administered to a selected subject group provides in said selected subject group an average SAMe AUC of at least about 8 ng·h/mL, at least about 8.5 ng·h/mL, at least about 9 ng·h/mL, at least about 9.5 ng·h/mL, or at least about 10 ng·h/mL per each 1 mg of SAMe ion. In preferred embodiments, the gallic acid ester is propyl gallate. Thus provide herein are compositions comprising SAMe and propyl gallate, wherein said compositions when administered to a selected subject group provides in said selected subject group an average SAMe AUC of at least about 8 ng·h/mL, at least about 8.5 ng·h/mL, at least about 9 ng·h/mL, at least about 9.5 ng·h/mL, or at least about 10 ng·h/mL per each 1 mg of SAMe ion. In some embodiments, the dose of SAMe ion delivered is at least 10 mg. In preferred embodiments, the dose of SAMe ion delivered is from 10 to 1600 mg.

In some embodiments, the term "selected subject group" is a group of selected human subjects. In some embodiments, a suitable "selected subject group" has six or more subjects who are dosed fasted. In some embodiments, all members of the "selected subject group" have pharmacokinetic parameters for SAMe that fall within statistically normal ranges (i.e. no outliers) and no member will be included on the basis of non-standard or unusual SAMe absorption or metabolism. In some embodiments, all members of the "selected subject group" are males. In other embodiments, the selected subject group is a group of selected non-human subjects. Preferably the non-human subjects are major food animals, companion animals or minor species animals. By "companion animals" it is meant to include animals such as, but not limited to, horses, dogs, and cats as recommended by the FDA. In some preferred embodiments, the composition when administered to a selected non-human subject group provides in said selected non-human subject group an average SAMe Cmax of at least about 1000 ng/mL, at least about 1500 ng/mL, at least about 2000 ng/mL, at least about 2500 ng/mL, at least about 3000 ng/mL, or at least about 3500 ng/mL per each 100 mg of SAMe ion. Thus provided herein are compositions comprising SAMe and propyl gallate, wherein administration of said compositions to a selected non-human subject group provides in said selected non-human subject group an average SAMe Cmax of at least about 1000 ng/mL, at least about 1500 ng/mL, at least about 2000 ng/mL, at least about 2500 ng/mL, at least about 3000 ng/mL, or at least about 3500 ng/mL per each 100 mg of SAMe ion.

In other preferred embodiments, the composition when administered to a selected subject group provides in said selected subject group an average SAMe Cmax of at least about 120 ng/mL and an average AUC of at least about 800 ng·h/mL per each 100 mg of SAMe ion for doses of SAMe ion of at least 100 mg. In some other preferred embodiments, the composition when administered to a selected subject group provides in said selected subject group an average SAMe Cmax of at least about 130 ng/mL and an average AUC of at least about 800 ng·h/mL per each 100 mg of SAMe ion for doses of SAMe ion of at least 100 mg. In still other preferred embodiments, the composition when administered to a selected subject group provides in said selected subject group an average SAMe Cmax of at least about 12 ng/mL and an average AUC of at least about 80 ng·h/mL per each 10 mg of SAMe ion for doses of SAMe ion of at least 10 mg. In some other preferred embodiments, the composition when administered to a selected subject group provides in said selected subject group an average SAMe Cmax of at least about 13 ng/mL and an average AUC of at least about 80 ng·h/mL per each 10 mg of SAMe ion for doses of SAMe ion of at least 10 mg. In other preferred embodiments, the composition when administered to a selected subject group provides in said selected subject group an average SAMe Cmax of at least about 1.2 ng/mL and/or an average AUC of at least about 8 ng·h/mL per each 1 mg of SAMe ion. In some other preferred embodiments, the composition when administered to a selected subject group provides in said selected subject group an average SAMe Cmax of at least about 1.3 ng/mL and/or an average AUC of at least about 8 ng·h/mL per each 1 mg of SAMe ion. In some embodiments, the dose of SAMe ion delivered is at least 10 mg. In preferred embodiments, the dose of SAMe ion delivered is from 10 to 3600 mg.

SAMe exemplary formulations comprising a gallic acid ester may also be configured to enable extended release of the formulated SAMe. Co-owned U.S. patent application 2009/0088404, which is incorporated herein by reference, provides novel formulations of extended-release SAMe formulations.

In some preferred embodiments, the composition comprises an oral delivery system, or a transdermal or transmucosal delivery system. In some embodiments, the composition comprises one of capsules or non-capsules (such as tablets, pastes, granules, caplets, lozenges, pastes, patches and suppositories). In some embodiments, the composition is a dietary or nutritional supplement. In some embodiments, the composition is a medical food.

In some exemplary embodiments, the composition is in a dosage form that comprises a functional coating and the functional coating constitutes from 1 to 20% of the total weight of the dosage form. In certain embodiments, the functional coating is comprised of one or more separate coatings or layers. In some embodiments, the one or more separate coatings or layers are each an enteric coating, a time-release coating, a pH-dependent coating, a seal coating or other as well as combinations of these. In preferred embodiments, one or more separate coatings or layers constitutes from 1 to 5%, 2 to 5%, 3 to 5%, or 4 to 5% of the total weight of the dosage form. Most preferably, one or more additional coating layers is an enteric coating which constitutes from 3-5% of the total weight of the unit dosage form.

Preferably, exogenous SAMe and the gallic acid ester are administered at the same time. Even more preferably, SAMe and the gallic acid ester are co-formulated. In some exemplary embodiments, the composition comprises SAMe and a gallic acid ester, wherein said SAMe and gallic acid ester are present in the core of the formulation. In other embodiments, the composition comprises SAMe and a gallic acid ester, wherein said gallic acid ester is present in one or more coating layers of the formulation.

Also provided herein is a method for improving the pharmacokinetic parameters of exogenous SAMe administered to a subject, said method comprising administering to the subject a non-parental composition comprising at least one physiologically effective dosage of SAMe in combination with at least one gallic acid ester selected to improve the pharmacokinetic parameters of said SAMe in a subject, said pharmacokinetic parameters measurable in the subject by one of a Cmax, an AUC, and combinations thereof in comparison to a control group administered the same or similar SAMe formulation yet lacking the gallic acid ester. For greater clarity all references to dose within this patent refer to dose as the dose of SAMe ion. Pharmacokinetic parameters such as average maximum plasma concentration of SAMe (Cmax) are determined using a bioanalytical method with adequate sensitivity, specificity, ruggedness, stability and repeatability (for example, a qualified liquid chromatography triple quad mass spectrometry based method coupled with a suitable extraction method for the separation of analyte from plasma). AUC values are preferably calculated from 0-24 hours using the trapezoid method and are uncorrected for baseline, endogenous SAMe levels. A suitable "selected subject group" or "selected non-human subject group" has six or more subjects. In some embodiments said "selected subject group" or "selected non-human subject group" are dosed fasted (preferably all male subjects). All members of the "selected subject group" or "selected non-human subject group" have pharmacokinetic parameters for SAMe that fall within statistically normal ranges (i.e. no outliers) and no member will be included on the basis of non-standard or unusual SAMe absorption or metabolism which may or may not result from a different genetic profile. The average Cmax values are derived by averaging the concentration at each time point for all members of the subject group. Use of methods in vivo provides superior Cmax and/or AUC values in comparison to conventional dosage forms of SAMe.

Some embodiments also relate to compositions and methods which yield a lower effective dose and/or less variable pharmacokinetic parameters (such as Tmax values with reduced variation) in comparison to conventional exogenous SAMe formulations or other SAMe formulations that lack a gallic acid ester ("SAMe control"). A "lower effective dose" or "reduced effective dose" is meant to define a physiologically acceptable dose of exogenous SAMe which results in pharmacokinetic parameters which are equivalent (or better) to a significantly higher dose of another SAMe formulation, such as that obtained through administration of a higher dose of one or more commercially available or "control" SAMe formulations. Formulations such as those provided herein which exhibit similar Cmax and AUC values at lower SAMe doses would have many benefits including a lower pill burden, increased rate of onset and/or potentially increased tolerability and/or compliance.

Additional embodiments also relate to compositions and methods which yield an improved side effect profile in comparison to conventional SAMe formulations. An "improved side effect" or "reduced side effect" or "beneficial side effect" profile is meant to define improved tolerability to administration of exogenous SAMe, such as less frequency and/or reduced intensity of side effects associated with SAMe supplementation. It is further recognized by the present investigators that any observed negative side effects associated with exogenous SAMe ion supplementation may be attributed to the SAMe counterion(s) present in the SAMe salts. By reducing the daily dose of exogenous SAMe ion needed to experience a positive therapeutic outcome, the corresponding significant reduction in SAMe counterion(s) may contribute to the improved side effect profile.

Some exemplary embodiments also relate to a dosing regimen of exogenous SAMe of once daily, or QD dosing, which results in improved pharmacokinetic profiles of SAMe in comparison to conventional twice daily or more frequent dosing. In certain embodiments, the effect of once a day dosing is believed to result in the most consistent pharmacokinetic parameter measurements, specifically those of the Cmax and Tmax. The less variable pharmacokinetic profiles that result from once a day dosing of formulations provided herein allow for more certainty of dosing and exposure by the medical practitioner as well as improved side effect profiles for subjects. Side effects include for example, nausea or stomach irritation, gastrointestinal upset, insomnia, headaches, irritation or possibly heart palpitations.

In some embodiments, formulations which exhibit superior pharmacokinetic profiles in comparison to conventional SAMe dosage forms, provide an improved rate of onset of SAMe which may result in enhanced therapeutic outcomes. Improved rate of onset is meant to mean the rate at which the subject experiences a positive outcome. For example, in Depression, the onset of antidepressant action is typically 4-6 weeks. SAMe formulations with improved pharmacokinetic profiles may be associated with corresponding improvement in therapeutic affect (e.g. antidepressant effect) in less than the typical or expected 4-6 weeks.

Other exemplary embodiments relate to methods for treating a disease or disorder in a subject and/or improving the nutritional status in a subject, said methods comprising administering to said subject compositions comprising physiologically effective dosages of exogenous SAMe in combination with one or more gallic acid ester thereby improving the pharmacokinetic profile of SAMe. Improved pharmacokinetic profiles are identified by, for example, an increase in Cmax and/or AUC values; or alternatively a decrease in effective dose; or pharmacokinetic parameters with reduced variation. Achieving one or more of these criteria would constitute an improvement in the pharmacokinetic profile of SAMe. Preferably, the gallic acid ester is propyl gallate.

In some embodiments, there is provided a method of treating or preventing a disease condition or disorder, comprising administering to a subject in need of such treatment an effective amount of a composition as described herein. In some embodiments, there is provided a method of treating in a patient a disease or disorder selected from the group consisting of mental and psychiatric disorders, nervous system diseases and disorders, neurological diseases and disorders, conditions associated with injuries to the central nervous system, liver diseases and disorders, cancers, joint diseases and disorders, inflammatory diseases and disorders, autoimmune diseases and disorders, degenerative diseases and disorders, soft-tissue diseases and disorders, pain diseases and disorders, cardiovascular disorders related to hyper-homocysteinemia and hypo-homocysteinemia, genetic disorders related to hyper-methylation and hypo-methylation, gastrointestinal diseases and disorders, atherosclerosis, Lesch-Nyhan disease, and disorders induced in whole or in part by oxidative or free-radical damage, comprising administering to the patient in need thereof a composition as described herein. In some embodiments, the subject is human.

Excipients and Processing Parameters Suitable for Use in the Invention

The product or dosage form characteristics which result from the processing methods and/or parameters for generating formulations such as tablets, include, but are not limited to, hardness, thickness, water content, friability, disintegration, dissolution profile(s), shape, size, weight, uniformity and composition. These product characteristics can be modulated in a number of ways and affect the final in vitro and/or in vivo performance of the formulations. As an example, tablets generated by compression or molding processes may have varying degrees of thickness or hardness depending on the processing parameters under which they were made. Product or dosage form characteristics may be a consequence of excipient selection, excipient composition, manufacturing methods applied or a combination of any of these. The combination of excipients as well as product characteristics (including processing methods or processing parameters) of the final dosage form will ultimately determine the pharmacokinetic profile of the active ingredient in vivo. The SAMe formulations of the invention may be processed or manufactured under specific conditions such as, for example, mixing methods (including sieve size, rpm, and milling), drying time, press conditions, environmental parameters (e.g. temperature and humidity) and combinations thereof. In order to quantitatively compare one tablet to another, it is customary to measure several of these product or dosage form characteristics. This is also necessary when attempting to duplicate multiple batches.

Excipients are usually grouped by their function such as: disintegrants, diluents, binders, lubricants, glidants, coatings, coloring agents or flavoring agents, and the same excipient may be used for more than one function in a given oral formulation. Commonly used pharmaceutically acceptable excipients include water, magnesium stearate, starch, lactose, microcrystalline cellulose, stearic acid, sucrose, talc, silicon dioxide, gelatin, acacia and dibasic calcium phosphate (Baldrick, P. (2000) *Regul. Toxicol. Pharmacol.* October 32(2): 210.) Excipients are combined with active ingredients for example to enhance appearance, improve stability, aid processing or aid disintegration after administration, but many other excipient functions are known in the art that can be applied to SAMe oral dosage forms. Classes of excipients which are often used and suitable for use in the present invention include but are not limited to, natural, modified-natural or synthetic mono-, oligo- or polysaccharides where oligo- and polysaccharides may or may not be physically or chemically crosslinked; natural, modified-natural or synthetic mono-, oligo- and polypeptides or proteins where oligo- and polypeptides and proteins may or may not be physically or chemically crosslinked; synthetic oligomers and polymers that may or may not be physically or chemically crosslinked; monomeric, hydrophobic, hydrophilic or amphoteric organic molecules; inorganic salts or metals; and combinations thereof.

Disintegrants

Disintegrants are added to non-parenteral formulations to induce breakup of the product or dosage form (i.e. tablet or capsule) when it comes in contact with aqueous fluid in order to help release the drug. The objectives behind addition of disintegrants are to increase surface area of the product fragments and to overcome cohesive forces that keep these particles together in a formulation. They do this by promoting wetting and swelling of the dosage form so that it breaks up in the gastrointestinal tract. Some binders such as starch and cellulose also act as disintegrants. Other disintegrants are clays, cellulose derivatives, algins, gums and crosslinked polymers. Another group of disintegrants called "super-disintegrants" are often utilized. These materials are effective at low (2-5%) concentrations. "Super-disintegrants" which may be suitable for use in the present invention include, but are not limited to, sodium starch glycolate (SSG), croscarmellose sodium or crosprovidone.

In some embodiments, compositions provided herein comprise SAMe and one or more gallic acid esters as well as one or more disintegrants or "super-disintegrants" which improve the pharmacokinetic profile of SAMe in vivo.

Binders

The binding material which holds the bulk of the product together and also helps maintain the product in a desired shape is known as a "binder" or "granulator". Binders suitable for use in the present invention are exemplified by, but are not limited to, sugars, gelatin, gums, microcrystalline cellulose and modified celluloses, waxes or synthetic polymers like polyethylene glycol or polyvinyl pyrrolidone. Some embodiments may include improved pharmacokinetic compositions comprising SAMe and one more gallic acid ester as well as one or more binders.

Lubricants

Additional excipients often utilized in product formulations are lubricants. These are substances which aid in the manufacturing process as they help minimize clumping of the products and also help release them from the manufacturing machinery. The most common "lubricant" used for oral formulations is magnesium stearate; however, other commonly used product lubricants include talc, calcium stearate, stearic acid (stearin), hydrogenated vegetable oils, sodium benzoate, leucine, carbowax 4000 and sodium stearyl fumarate all of which may be suitable for use in the present invention. Further exemplary embodiments also relate to improved pharmacokinetic compositions comprising SAMe and one or more gallic acid esters and one or more lubricants.

Glidants

Glidants also referred to as "flow-aids", help to keep the powder making up the products flowing as the products are being made, stopping them from forming lumps. Examples of commonly used glidants which may be suitable for use in the invention include colloidal silicon dioxide, talc, calcium silicate and magnesium silicate. Additional embodiments relate to improved pharmacokinetic compositions comprising SAMe and one or more gallic acid esters and one or more glidants.

The suitability of a particular excipient, such as, for example, a "matrix material", "disintegrant", "super-disintegrant" "binder", "lubricant", "glidant", or "coating" may be identified by analyzing the in vivo pharmacokinetics of formulations containing the excipient, gallic acid ester and SAMe. Alternatively, in vitro analysis of one or more excipients using a series of standard in vitro techniques which are well known in the art may be used to pre-screen excipients and ultimately provide a means to predict in vivo pharmacokinetic profiles. Furthermore, the use of references in the art may also provide insight into potentially suitable pharmaceutically or nutritionally acceptable excipients (such as a "matrix material", "disintegrant", "binder", "lubricant", "glidant", or "coating") for use in the present invention. Preferably, in vitro analysis of one or more excipients using dissolution studies conducted with a buffer pH of 6.8 or less may be used to pre-screen excipients and ultimately provide a means to predict in vivo pharmacokinetic profiles.

Processing Methods and Parameters

Processing methods and/or parameters which may be modified in order to improve the pharmacokinetic profile and/or alter the dissolution profile of SAMe-gallic acid ester formulations include but are not limited to: relative humidity, temperature, drying time and other environmental parameters.

The present embodiments are further described by the following examples. These examples, while illustrating certain specific aspects of the present embodiments, should not be considered to limit or circumscribe the scope of the disclosed embodiments.

EXAMPLES

Example 1

Propyl Gallate Significantly Increases Plasma Levels of Exogenously Administered SAMe Tablets comprising SAMe and various alkyl gallates of different chemical structure were generated by mixing SAMe with either methyl gallate, ethyl gallate, butyl gallate, isobutyl gallate, isoamyl gallate or octyl gallate (see structures below). Tablets were then administered to Beagle dogs and blood samples were withdrawn over time. Analysis of concentrations of SAMe in plasma was used to compare the effects of these gallic acid esters on the uptake of orally administered SAMe in the blood.

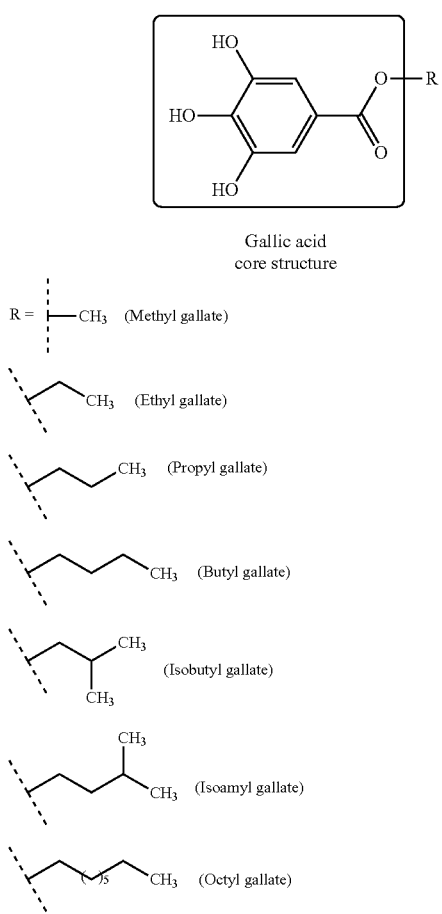

Gallic acid core structure

R = —CH₃ (Methyl gallate)

(Ethyl gallate)

(Propyl gallate)

(Butyl gallate)

(Isobutyl gallate)

(Isoamyl gallate)

(Octyl gallate)

Tablets were generated by mixing 400 mg SAMe ion (from SAMe disulfate tosylate) with 25 mg gallic acid ester along with excipients (microcrystalline cellulose, sodium starch glycolate, silicon dioxide, and magnesium stearate) to make up the 1025 mg tablet. A commercial seal coat and then a commercial enteric coat was applied to the tablets prior to dissolution testing. Detailed dissolution profiling was performed according to USP standards at either pH 6.8 or 6.0 on each set of tablets to ensure that adequate dissolution was achieved prior to in vivo pharmacokinetic analysis.

For in vivo studies, fasted male beagle dogs (7-10 kg) were used. The study protocol was approved by the institution's Animal Care Committee, and all animals were cared for according to regulations proposed by Agriculture Canada and the USDA. Each group (consisting of 6 dogs) was dosed with a single orally administered enteric coated tablet, under fasted conditions, followed by 5 mL of purified water orally with a syringe to facilitate swallowing. Blood samples (2 mL each) for SAMe analysis were collected from the jugular vein using the following time points: pre-dose, 20 and 40 minutes, 1, 1.5, 2, 3, 4, 6, and 8 hours after treatment. The venipuncture blood samples were collected into tubes containing the anticoagulant K2-EDTA, and stored on wet ice pending processing. Following collection, samples were centrifuged (at 4° C.) to separate the plasma fraction from the blood cells. The resulting plasma fraction was recovered and stored frozen (at −80° C.) using polypropylene tubes pending bioanalytical analysis.

The concentration of SAMe in dog plasma was determined using a well established liquid chromatography-tandem mass spectrometry (LC/MS/MS) method. This method employs stable-isotope dilution liquid chromatography-electrospray injection tandem mass spectrometry (LC-ESI-MS/MS) to determine SAMe and SAH in plasma. The analysis used to calculate the main pharmacokinetic parameters (Cmax, Tmax and AUC) was conducted using GraphPad Prism® 5 software.

Ten different formulations were tested in the present study. 400 mg SAMe co-formulated with 25 mg propyl gallate was compared to: SAMe control tablets (i.e., with no propyl gallate); SAMe tablets co-administered with separate 25 mg propyl gallate tablets; a commercially available SAMe product (400 mg); or 400 mg SAMe with 25 mg of either methyl gallate, ethyl gallate, butyl gallate, isobutyl gallate, isoamyl gallate or octyl gallate.

The graph in FIG. 1 clearly shows the superior combination of SAMe and ethyl gallate, propyl gallate, isoamyl gallate or octyl gallate. The maximum SAMe plasma concentration of these 10 formulations identifies for the first time that SAMe co-formulated with either ethyl gallate, propyl gallate, isoamyl gallate or octyl gallate has superior uptake into the plasma as compared to the other gallic acid ester formulations tested. Surprisingly, administration of SAMe with alkyl gallates whose alkyl moiety differs by as little as one carbon (e.g. butyl gallate) did not result in pharmacokinetics even close to that of SAMe-propyl gallate formulations.

Example 2

Beagle Plasma SAMe Levels in the Presence of Gallate-Related Molecules

In vivo experiments similar to those conducted in Example 1 were also performed using SAMe compositions comprising butylated hydroxytoluene (BHT), propyl paraben or gallic acid, all of which are agents that are well-known to be structurally similar to propyl gallate. BHT, propyl paraben and propyl gallate are food-grade antioxidants which have often been used in combination. These agents are structurally similar as seen here:

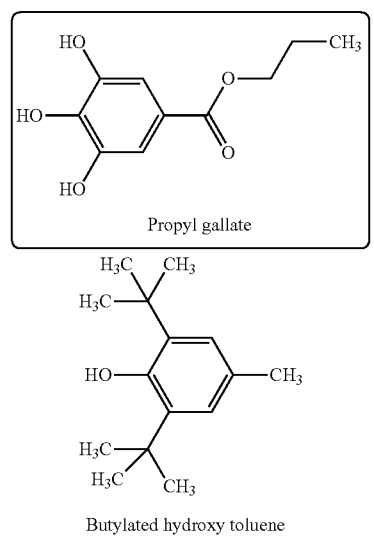

Propyl gallate

Butylated hydroxy toluene

-continued

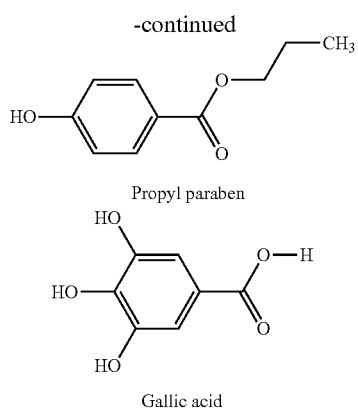

Propyl paraben

Gallic acid

Capsules comprising 100 mg of either butylated hydroxytoluene, propyl paraben, gallic acid or propyl gallate were formulated using size #000 gelatin capsules, each containing 100 mg of SAMe ion. The capsules also contained additional excipients (Microcrystalline cellulose, Sodium Starch Glycolate, Colloidal Silicon Dioxide, and Magnesium Stearate). Capsules were manually filled and in some embodiments, a layer of commercial seal coat was applied to the capsules using a fluid bed coater.

Beagle dogs were administered a single orally delivered dose as described above. SAMe control capsules contained 100 mg of SAMe ion and no propyl gallate.

Figure 2A:
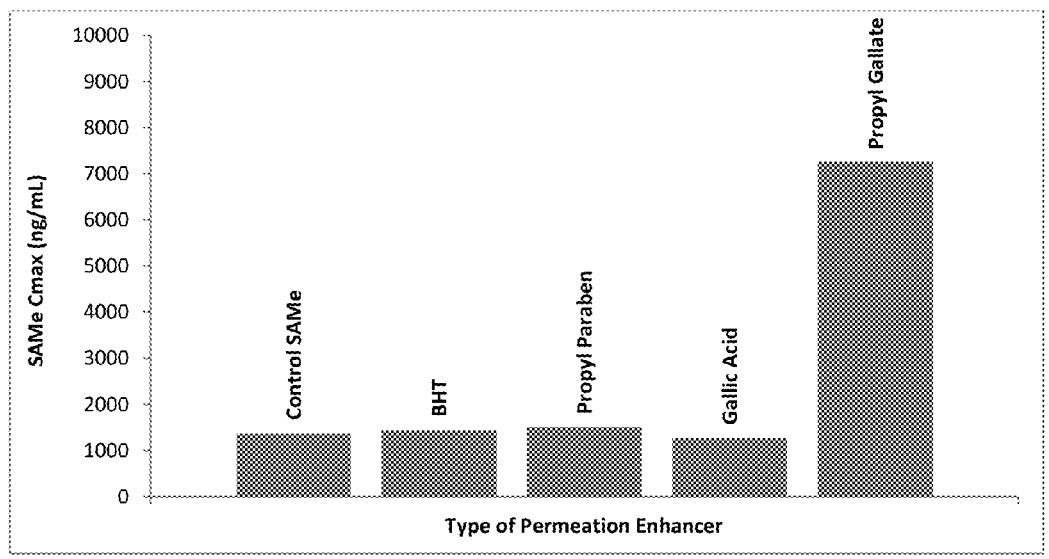
FIG. 2A is a graph showing the average maximum SAMe plasma concentration (Cmax) of beagles administered a single capsule containing 100 mg SAMe ion alone ("Control SAMe") or co-formulated with 100 mg of one of the following: butylated hydroxytoluene ("BHT"), propyl paraben or gallic acid.
Figure 2B:
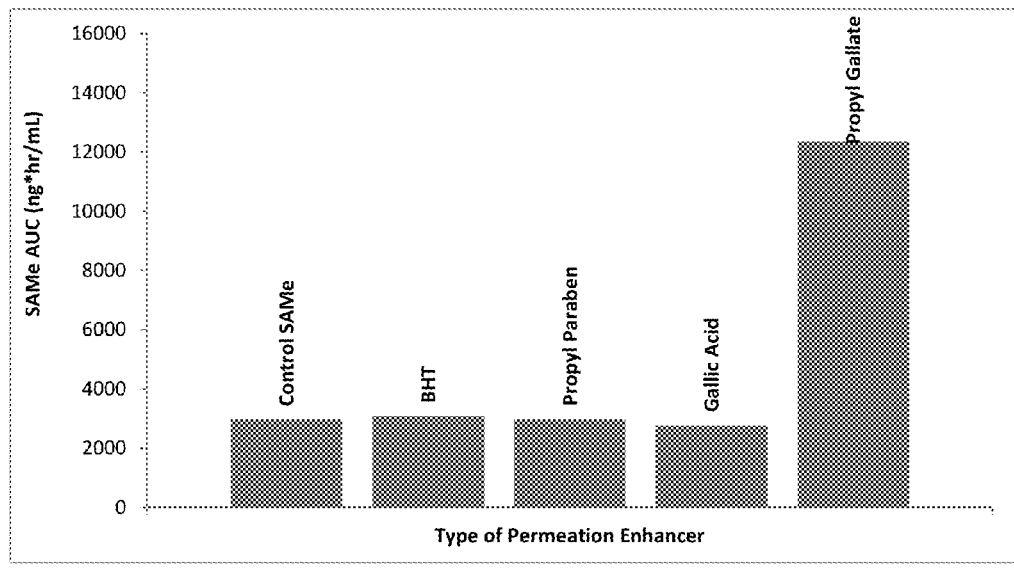
FIG. 2B is a graph showing the average SAMe plasma area under the curve (AUC) of beagles administered a single capsule containing 100 mg SAMe ion alone ("Control SAMe") or co-formulated with 100 mg of one of the following: butylated hydroxytoluene ("BHT"), propyl paraben or gallic acid.

The graphs in FIGS. 2A and 2B show the plasma SAMe Cmax and AUC, respectively, from each formulation and clearly present the superior and surprising ability of propyl gallate to increase SAMe uptake into the blood in comparison to the structurally similar butylated hydroxytoluene (BHT), propyl paraben and gallic acid.

Example 3

Effects of Propyl Gallate Dose on SAMe Uptake in Caco-2 Cell Transport

In vitro experiments on permeability of SAMe across Caco-2 cell monolayers treated with propyl gallate were conducted to identify levels of propyl gallate which increase the amount of SAMe absorbed by the Caco-2 cells in comparison to untreated Caco-2 cell monolayers. The Caco-2 cell line is derived from a human colorectal carcinoma and is widely used for in vitro cell culture models for the study of gastrointestinal drug absorption (Stewart, B., (1995) *Pharm. Res.* 12:693). In these models, pure cell lines are grown on a semi-permeable membrane. Drug formulations are placed on the apical or basolateral side of the cell monolayer and transport is determined via measurement of drug concentrations on the other side of the membrane.

The Caco-2 cell line utilized here was from the American Type Culture Collection (ATCC). Caco-2 cells are grown in Dulbecco's modified Eagle's medium (DMEM, Gibco) supplemented with 20% FBS (fetal bovine serum, Gibco), 100 uM non-essential amino acids (NEAA, Gibco) and 2 mM L-glutamine (Gibco). A Beckton Dickinson BIOCOAT® HTS Caco-2 Assay System Kit was used resulting in $6.6 \times 10^5$ cells/cm$^2$ seeding density (BIOCOAT is a registered trademark of Collaborative Biomedical Products, Inc., Bedford, Mass., USA). The cells used in transport studies were grown for 3 days before the experiments. The culturing conditions were 37° C. in an atmosphere of 5% $CO_2$ and 100% humidity.

For permeability across Caco-2 cell monolayers, the transport medium used was Hank's Buffered Salt Solution (HBSS; purchased from Gibco) containing D-glucose, and HEPES pH adjusted to 7.4. A 2 mM aqueous solution of SAMe disulfate tosylate was added on the apical or basolateral side according to the manufacturer's procedure for the Caco-2 kit. Samples were measured after a 120-minute incubation by liquid chromatography-mass spectrometry (LC/MS). The integrity of the monolayers was monitored using Lucifer Yellow Assay.

The permeability (Papp) of SAMe is calculated using the following formula:

$$Papp = \frac{\frac{dQ}{dt}}{C_0 A}$$

Where $dQ/dt$ is the rate of permeation, $C_0$ is the initial concentration of test agent, and A is the area of the monolayer.

SAMe absorption in Caco-2 cells was measured for two commonly used SAMe salts. The absorption was low for both SAMe salts (SAMe disulfate tosylate; SAMe 1,4 butanedisulfonate) as evidenced by a low apparent permeability coefficients (Papp=$0.41 \times 10^{-6}$ and $0.50 \times 10^{-6}$ cm s$^{-1}$, respectively, in apical to basolateral and basolateral to apical directions, respectively for SAMe disulfate tosylate; and Papp=$0.50 \times 10^{-6}$ and $0.60 \times 10^{-6}$ cm s$^{-1}$ in apical to basolateral and basolateral to apical directions, respectively for SAMe 1,4 butanedisulfonate. The results in Table 1 below show the absorption of SAMe disulfate tosylate in the presence of various concentrations of propyl gallate.

TABLE 1

| | | Permeability of SAMe in the Presence of Propyl Gallate (Caco-2 Cell Model) | | |
|---|---|---|---|---|
| Test Article | Excipient | Average Permeability Coefficient ($\times 10^{-4}$ cm/s) Apical→ Basolateral | Average Permeability Coefficient ($\times 10^{-4}$ cm/s) Basolateral→ Apical | Average TEER Resistance 19-hr post assay (ohms) |
| SAMe 2 mM | Propyl Gallate 0 mM | 0.016 | 0.017 | 6200 |
| SAMe 2 mM | Propyl Gallate 0.2 mM | 0.016 | Not determined | 5350 |
| SAMe 2 mM | Propyl Gallate 2 mM | 0.43 | Not determined | 3250 |

As shown in Table 1, propyl gallate increases SAMe transport in Caco-2 cells with good TEER recovery at the increased concentration.

Example 4

Effects of Propyl Gallate on SAMe Transport Using the PAMPA Model

Using a PAMPA (parallel artificial membrane permeability assay) model, the permeability of SAMe was measured in the presence and absence of propyl gallate. PAMPA models have been developed to exhibit a high degree of correlation with permeation across a variety of barriers, including the gastrointestinal tract. They are important here because these membranes do not comprise tight junctions, in contrast to the Caco-2 cell monolayer, and thus do not allow for paracellular transport.

PAMPA methods were used to determine the permeability of substances from a donor compartment, through a lipid-infused artificial membrane into an acceptor compartment. A multi-well microtitre plate was used for the donor and a membrane/acceptor compartment is placed on top. At the beginning of the test, SAMe disulfate tosylate (with or without different concentrations of propyl gallate as indicated in Table 2 below) was added to the donor compartment, and the acceptor compartment remained drug-free. After an incubation period, the compartments were separated and the amount of SAMe was measured in each compartment. Mass balance allows calculation of SAMe that remains in the membrane.

As seen in Table 2, SAMe showed essentially no transport across the PAMPA membrane and the presence of propyl gallate at 2.0 mM had no effect on SAMe transport. This is opposite to the effect of propyl gallate on SAMe using the Caco-2 cell transport model.

The artificial PAMPA membrane is a non-cellular lipid bilayer configured as a barrier, and experiments involving PAMPAs measure passive transport of molecules across this barrier, from one side to another. The fact that propyl gallate does not enhance permeability of SAMe across the PAMPA membrane means that the mechanism of enhancement is not through passive intracellular transport. The mechanism is therefore more likely to involve cellular components missing from the PAMPA model, such as tight junctions or active transport. Involvement of active transport via cell-based transporters was not supported by the Caco-2 cell model which showed that SAMe permeability from Apical to Basolateral was identical to permeability from Basolateral to Apical (see Table 1). Since epithelial cell transporter expression is typically localized to one direction or the other, the lack of a favored direction for permeability argues against intracellular active transport. That data is, however, consistent with a paracellular (tight junction) based mechanism of SAMe transport.

The fact that propyl gallate does not enhance the transport of other drugs known to be transported paracellularly (e.g. metformin or ranitidine—see Example 5 below) implies that the interaction of propyl gallate and SAMe is specific. Without being bound by any particular theory, based on the data, propyl gallate enhances the absorption of SAMe in a specific fashion with the route of transport involving tight junctions.

TABLE 2

Permeability of SAMe in the Presence of Propyl Gallate

| Test Article | Excipient | Average Effective Permeability ($\times 10^{-6}$ cm/s) | Assay Duration (hr) | % Recovery |
|---|---|---|---|---|
| SAMe 2 mM | Propyl Gallate 0 mM | 0.0042 | 5 | 114 |
| SAMe 2 mM | Propyl Gallate 0.2 mM | 0.0020 | 5 | 116 |
| SAMe 2 mM | Propyl Gallate 2 mM | 0.0048 | 5 | 116 |

Example 5

Effects of Propyl Gallate on the In Vitro Transport of Ranitidine and Metformin

Experiments similar to those conducted in Example 3 above were also performed using propyl gallate and either Ranitidine or Metformin, both of which have known paracellular intestinal transport mechanisms (Bourdet and Thakker, *Pharm. Res.* (2006) June; 23(6):1165-77 and Proctor, W. R. et al., *Drug. Metab. Dispos.* (2008) August; 36(8):1650-8).

For permeability across Caco-2 cell monolayers, the transport medium used was also Hank's Buffered Salt Solution (HBSS; purchased from Gibco) containing D-glucose, and HEPES pH adjusted to 7.4. Aqueous solutions of ranitidine or metformin (2 mM) containing 0 mM, 0.2 mM or 2.0 mM propyl gallate were added on the apical or basolateral side according to the manufacturer's procedure for the Caco-2 kit. Samples were measured after a 120 minute incubation using liquid chromatography-mass spectrometry (LC/MS). The integrity of the monolayers was monitored using Lucifer Yellow Assay.

As shown in Table 3 below, the presence of propyl gallate did not increase the rate of transport across the Caco-2 cell monolayer for either ranitidine or metformin, as it did with SAMe tosylate.

TABLE 3

Permeability of Ranitidine and Metformin in the Presence of Propyl Gallate

| Test Article | Test Concentration (µM) | Assay Duration (hr) | Average Effective Permeability ($\times 10^{-6}$ cm/s) |
|---|---|---|---|
| Metformin (2.0 mM) | 2000 | 2 | 0.18 |
| Metformin (2.0 mM) + propyl gallate (0.2 mM) | 2000 | 2 | 0.22 |
| Metformin (2.0 mM) + propyl gallate (2.0 mM) | 2000 | 2 | 0.26 |
| Ranitidine (2.0 mM) | 2000 | 2 | 0.34 |
| Ranitidine (2.0 mM) + propyl gallate (0.2 mM) | 2000 | 2 | 0.28 |
| Ranitidine (2.0 mM) + propyl gallate (2.0 mM) | 2000 | 2 | 0.25 |

Example 6

Beagle Plasma SAMe Levels are Increased in the Presence of Various Doses of Propyl Gallate Tablets comprising SAMe and various amounts of propyl gallate were generated by mixing S-adenosyl-L-methionine disulfate tosylate granules (equivalent to 400 mg of SAMe ion) with the various amounts of propyl gallate listed in Table 4 below. Each mixture was pressed into a tablet and coated followed by dissolution profiling and in vivo pharmacokinetic analysis using beagle dogs.

Dissolution profiling was performed according to USP standards with either pH 6.0 or pH 6.8 buffers to ensure adequate tablet dissolution prior to administration to dogs.

The concentration of SAMe in dog plasma was determined using the well established LC/MS/MS method. This method employs stable-isotope dilution liquid chromatography-electrospray injection tandem mass spectrometry (LC-ESI-MS/MS) to determine SAMe and SAH in plasma. The analysis used to calculate the main pharmacokinetic parameters (Cmax, Tmax and AUC) was conducted using GraphPad Prism® 5 software.

As seen in Table 4 below, the maximum SAMe plasma concentration (Cmax) and AUC levels were significantly higher in formulations comprising all levels of propyl gallate in comparison to the control tablets of the SAMe salt alone. Surprisingly, the SAMe plasma concentration levels were also significantly higher when 400 mg SAMe ion was combined with as little as 6.25 mg of propyl gallate representing a 1:64 weight ratio of propyl gallate to SAMe.

TABLE 4

| Tablets comprising SAMe plus decreasing amounts of propyl gallate | | | | | | |
|---|---|---|---|---|---|---|
| SAMe Dose, mg | Propyl Gallate, mg | $T_{max} \pm$ SD, hrs | Cmax average of individuals, ng/mL | $AUC_{(0-t)}$, hr * ng/mL | $AUC_{(0-inf.)} \pm$ SD, hr * ng/mL | $T_{1/2} \pm$ SD, hrs |
| 400 | 100 | 1.6 ± 0.7 | 18,700 | 34,078 | 34,305 ± 18,484 | 1.0 ± 0.2 |
| 400 | 25 | 1.2 ± 0.5 | 15,333 | 24,847 | 25,159 ± 13,033 | 1.5 ± 0.4 |
| 400 | 0 | 1.8 ± 0.7 | 6731 | 14,756 | 15,186 ± 6,831 | 1.4 ± 0.4 |
| 400 | 6.25 | 1.4 ± 0.8 | 11,269 | 21,395 | 21,734 ± 9848 | 1.4 ± 0.5 |

The dissolution test method used is typically as follows:
USP Apparatus II operated at 100 RPM,
Fluid Phase: 1 L USP Simulated Gastric Fluid without enzyme, pH 1.2, 37° C.,
Aqueous Buffer Phase—1 L USP simulated Intestinal Fluid without enzyme, pH 6.8 or pH 6.0, 37° C.,
Tablets are exposed to the acid phase for two hours then transferred to the Buffer Phase,
Aliquots are drawn following exposure to the acid phase for 2 hours, then at prescribed intervals while in the buffer phase,
Samples are diluted 1→10 with n/10 HCL, and
Drug concentration is determined spectrophotometrically at 258 mm.

For in vivo studies, fasted male beagle dogs (7-10 kg) were used as described above. Each group (6 dogs for SAMe/propyl gallate and 6 dogs for the SAMe control lacking propyl gallate) were dosed with a single orally administered enteric coated tablet, under fasted conditions, followed by 5 mL of purified water orally with a syringe to facilitate swallowing. Pharmacokinetic blood samples (2 mL each) for SAMe analysis were collected from the jugular vein using the following time points: pre-dose, 20 and 40 minutes, 1, 1.5, 2, 3, 4, 6, and 8 hours after treatment. The venipuncture blood samples were collected into tubes containing the anticoagulant K2-EDTA, and stored on wet ice pending processing. Following collection, samples were centrifuged (at 4° C.) to separate the plasma fraction from the blood cells. The resulting plasma fraction was recovered and stored frozen (at −80° C.) using polypropylene tubes pending bioanalytical analysis.

These results demonstrate the surprising and dramatic increase in SAMe uptake in the presence of minimal amounts of propyl gallate.

Example 7

Propyl Gallate Significantly Increases Human Plasma Levels of Exogenous SAMe A Phase I clinical study was carried out using tablets comprising SAMe and propyl gallate. Dose escalation of SAMe from 400 mg to 1600 mg was conducted using healthy, human volunteers. These SAMe-propyl gallate formulations were compared to one of the most commonly used commercially available SAMe products on the market which has been extensively studied in other SAMe clinical trials.

1025 mg tablets were generated by mixing 400 mg SAMe ion with 25 mg propyl gallate along with excipients to make up the 1025 mg (microcrystalline cellulose, sodium starch glycolate, silicon dioxide, and magnesium stearate). A seal coat and then enteric coat was applied to the tablets prior to dissolution testing and administration to human subjects—the exemplary formulation is referred to as the "MSI Formulation". These tablets comprising SAMe and propyl gallate had significantly higher Cmax and AUC values compared to the commercial product.

Table 5 show the plasma Cmax and AUC values for patients treated with 400 mg, 800 mg or 1600 mg of the MSI Formulation.

TABLE 5

Comparison of 400 mg, 800 mg and 1600 mg of SAMe ion in MSI Formulation

|  | MSI Formulation @ 400 mg SAMe ion[1] | MSI Formulation @ 800 mg SAMe ion | MSI Formulation @ 1600 mg[2] SAMe ion |
|---|---|---|---|
| Cmax, ng/mL | 1045 | 3255 | 4809 |
| AUC, ng hrs/mL | 4644 | 9361 | 16511 |
| Tmax, hrs | 7.75 | 3.0 | 3.25 |

[1]Using 6 evaluable subjects;
[2]Using 7 evaluable subjects

Figure 3A:
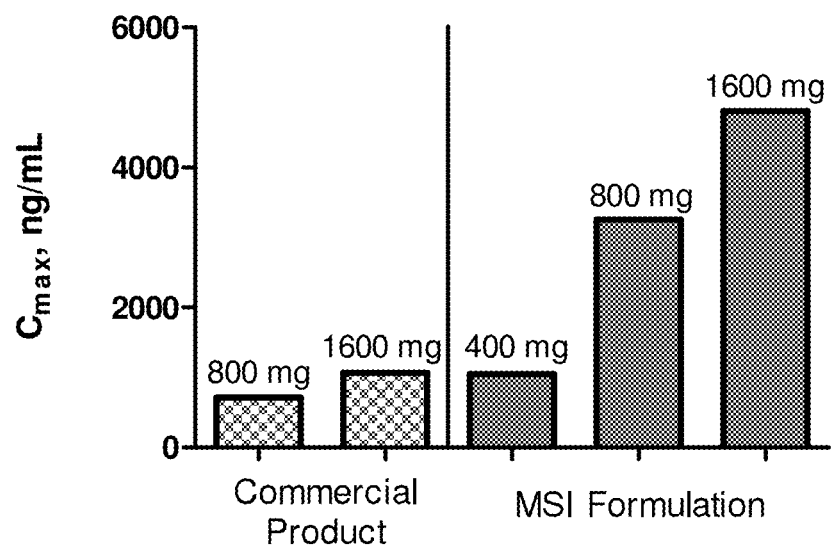
FIG. 3A is a graph showing the average maximum SAMe plasma concentration (Cmax) of human subjects administered a single dose of either 400 mg, 800 mg or 1600 mg of the MSI Formulation (SAMe and propyl gallate) or a 1600 mg dose of the commercial SAMe product.
Figure 3B:
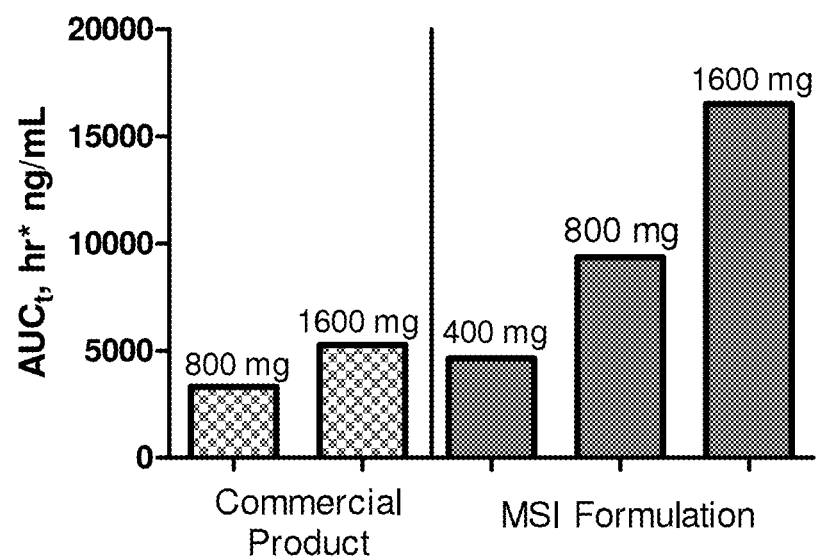
FIG. 3B is a graph showing the average SAMe plasma area under the curve (AUC) of human subjects administered a single dose of either 400 mg, 800 mg or 1600 mg of the MSI Formulation (SAMe and propyl gallate) or a 1600 mg dose of the commercial SAMe product.

The human plasma Cmax and AUC values of 400, 800 and 1600 mg of the MSI Formulation doses are graphed in comparison to the 800 and 1600 mg dose of the commercially available SAMe product which does not contain propyl gallate. As seen in both FIGS. 3A and 3B, at both 400 mg and 1600 mg dosages, the Cmax and AUC values of the MSI Formulation were significantly higher than those of the commercially available SAMe product. Also, the 400 mg dose of the MSI Formulation (containing SAMe and propyl gallate) achieved results comparable to a 1600 mg dose of the commercial product. Thus, lower dosages of SAMe-propyl gallate formulations are needed to achieve equivalent pharmacokinetics of the commercially available SAMe products.

These results further demonstrate the unexpected and significant benefits of using even low doses of propyl gallate in SAMe formulations.

Example 8

Gender Effect Evaluation of SAMe Compositions

There are multiple effects from administration of exogenous SAMe and many are known to be gender specific. There are various other theories to explain the gender difference in exogenous SAMe pharmacokinetics including larger body size and blood volume of males in general; higher body mass index (BMI) and different methylation states between the two sexes as well as the presence of particular genetic polymorphisms.

In order to assess the effects of gender on the MSI Formulation, a Phase I clinical study was carried out using tablets comprising SAMe and propyl gallate. 800 mg was administered to healthy, human volunteers (7 male, 17 female) as described above. The pharmacokinetic profile of these SAMe-propyl gallate formulations was also compared to the control commercial product as above.

1025 mg tablets were generated by mixing 400 mg SAMe ion with 25 mg propyl gallate along with excipients to make up the 1025 mg (microcrystalline cellulose, sodium starch glycolate, silicon dioxide, and magnesium stearate). A seal coat and then enteric coat was applied to the tablets prior to dissolution testing and administration to human subjects—the exemplary formulation is referred to as the "MSI Formulation". These tablets comprising SAMe and propyl gallate had significantly higher Cmax values compared to the commercial product.

The average maximum SAMe plasma concentration (Cmax) for male and female subjects treated with 800 mg of the MSI Formulation was 3832±927 ng/mL and 3054±580 ng/mL respectively (Average Cmax±Standard Error). Surprisingly, the MSI Formulation showed no significant difference in values between the two groups indicating that the MSI Formulation is able to overcome the known gender differences in SAMe pharmacokinetic values and thus significantly increase the SAME plasma levels equally well in both males and females.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A composition comprising exogenous S-adenosylmethionine and at least one gallic acid ester, wherein said gallic acid ester is selected from the group consisting of ethyl gallate, propyl gallate, and octyl gallate.

2. The composition of claim 1, wherein the ratio (weight:weight) of gallic acid ester to exogenous S-adenosylmethionine ion is from 5:1 to 1:400.

3. The composition of claim 2, wherein the ratio (weight:weight) of gallic acid ester to exogenous S-adenosylmethionine ion is from 1:1 to 1:100.

4. The composition of claim 3, wherein the ratio (weight:weight) of gallic acid ester to exogenous S-adenosylmethionine ion is from 1:2 to 1:80.

5. The composition of claim 1, wherein said composition comprises from about 1 to about 400 mg of said gallic acid ester.

6. The composition of claim 5, wherein said composition comprises from about 5 to about 200 mg of gallic acid ester.

7. The composition of claim 6, wherein said composition comprises from about 5 to about 100 mg of gallic acid ester.

8. The composition of claim 1, wherein said composition comprises 0.1 to 40%, 0.1 to 25%, or 0.1 to 10% by weight gallic acid ester.

9. The composition of claim 1, wherein the dose of exogenous S-adenosylmethionine ion is from about 50 mg to about 1600 mg.

10. The composition of claim 1, wherein the composition comprises an oral dosage form.

11. The composition of claim 10, wherein the oral dosage form comprises a functional coating.

* * * * *